US009096483B2

(12) United States Patent
Bhattacharyya et al.

(10) Patent No.: US 9,096,483 B2
(45) Date of Patent: Aug. 4, 2015

(54) CATALYTIC ISOMERIZATION OF HEXANES USING IONIC LIQUIDS

(71) Applicant: UOP LLC, Des Plaines, IL (US)

(72) Inventors: Alakananda Bhattacharyya, Glen Ellyn, IL (US); Stuart Smith, Lake Zurich, IL (US); Dana K. Sullivan, Mount Prospect, IL (US); Susie C. Martins, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/311,984

(22) Filed: Jun. 23, 2014

(65) Prior Publication Data
US 2015/0005546 A1    Jan. 1, 2015

Related U.S. Application Data

(63) Continuation-in-part of application No. 13/931,765, filed on Jun. 28, 2013.

(51) Int. Cl.
*C07C 5/27* (2006.01)
*C07C 6/08* (2006.01)
*C07C 6/10* (2006.01)

(52) U.S. Cl.
CPC .............. *C07C 6/10* (2013.01); *C07C 2527/125* (2013.01); *C07C 2527/14* (2013.01)

(58) Field of Classification Search
USPC .......................... 585/745, 740, 741, 743, 708
See application file for complete search history.

(56) References Cited

U.S. PATENT DOCUMENTS

| 5,233,121 | A | 8/1993 | Modica |
| 5,750,455 | A | 5/1998 | Chauvin et al. |
| 6,235,959 | B1 | 5/2001 | Hirschauer et al. |
| 6,288,281 | B1 | 9/2001 | Nemeth et al. |
| 6,623,659 | B2 | 9/2003 | Munson et al. |
| 6,797,853 | B2 | 9/2004 | Houzvicka et al. |
| 7,053,261 | B2 | 5/2006 | Herbst et al. |
| 7,285,698 | B2 | 10/2007 | Liu et al. |
| 7,432,408 | B2 | 10/2008 | Timken et al. |
| 7,432,409 | B2 | 10/2008 | Elomari et al. |
| 7,482,501 | B2 | 1/2009 | Leitner et al. |

(Continued)

FOREIGN PATENT DOCUMENTS

| CN | 102924213 A | 2/2013 |
| EP | 1 346 768 B1 | 9/2003 |

(Continued)

OTHER PUBLICATIONS

Huibin et al., "Reaction performance and . . . ," Catalysis Communications, v 12, n 3, p. 180-183, Nov. 30, 2010.

(Continued)

*Primary Examiner* — Thuan D Dang

(57) ABSTRACT

Processes for the disproportionation and isomerization of a hydrocarbon feed using a liquid catalyst comprising an ionic liquid and a carbocation promoter are described. The ionic liquid is unsupported, and the reactions occur at temperatures below the decomposition temperature of the ionic liquid, typically below about 250° C. The process includes isomerizing a hydrocarbon feed comprising normal $C_6$ alkane or branched $C_6$ alkane by contacting the hydrocarbon feed with a liquid catalyst in a reaction zone to form a product mixture. Isomerization reaction mixtures are also described.

12 Claims, 2 Drawing Sheets

(56) References Cited

U.S. PATENT DOCUMENTS

| | | |
|---|---|---|
| 7,495,144 B2 | 2/2009 | Elomari |
| 7,531,707 B2 | 5/2009 | Harris et al. |
| 7,902,417 B2 | 3/2011 | Goldman et al. |
| 7,915,468 B2 | 3/2011 | Timken et al. |
| 8,183,425 B2 | 5/2012 | Luo et al. |
| 8,187,994 B2 | 5/2012 | Harris |
| 8,198,494 B2 | 6/2012 | Elomari et al. |
| 8,198,499 B2 | 6/2012 | Luo et al. |
| 8,222,471 B2 | 7/2012 | Elomari et al. |
| 8,247,628 B2 | 8/2012 | Hommeltoft et al. |
| 8,288,601 B2 | 10/2012 | Hommeltoft et al. |
| 8,319,001 B2 | 11/2012 | Hommeltoft |
| 2003/0109767 A1 | 6/2003 | Vasina et al. |
| 2003/0181780 A1 | 9/2003 | Herbst et al. |
| 2003/0196931 A1 | 10/2003 | Houzvicka et al. |
| 2004/0059173 A1 | 3/2004 | Houzvicka et al. |
| 2004/0077914 A1 | 4/2004 | Zavilla et al. |
| 2005/0033102 A1 | 2/2005 | Randolph et al. |
| 2009/0171133 A1 | 7/2009 | Luo et al. |
| 2010/0147746 A1* | 6/2010 | Driver et al. ............ 208/97 |
| 2011/0105811 A1 | 5/2011 | O'Rear et al. |
| 2011/0105820 A1 | 5/2011 | Harris |
| 2011/0137098 A1 | 6/2011 | Tschirschwitz et al. |
| 2011/0184219 A1 | 7/2011 | Timken et al. |
| 2011/0319693 A1 | 12/2011 | Hommeltoft et al. |
| 2011/0319694 A1 | 12/2011 | Timken et al. |
| 2012/0165590 A1 | 6/2012 | Liu et al. |
| 2012/0165593 A1 | 6/2012 | Liu et al. |
| 2012/0172647 A1 | 7/2012 | Liu et al. |
| 2012/0178982 A1 | 7/2012 | Liu et al. |
| 2012/0264605 A1 | 10/2012 | Rogers et al. |
| 2012/0282150 A1 | 11/2012 | Timken et al. |
| 2013/0062253 A1 | 3/2013 | Timken |
| 2013/0066121 A1 | 3/2013 | Zhan et al. |
| 2013/0066130 A1 | 3/2013 | Luo et al. |

FOREIGN PATENT DOCUMENTS

| | | |
|---|---|---|
| EP | 2 520 558 A1 | 11/2012 |
| EP | 2 597 078 A1 | 5/2013 |
| GB | 1118897 A | 7/1968 |
| JP | 2011098924 A2 | 5/2011 |
| WO | WO 00/40673 | 7/2000 |

OTHER PUBLICATIONS

Zinurov et al., "Skeletal Isomerization of . . . ," Petroleum Chemistry, v 50, n 5, p. 376-380, Sep. 2010.

Petre et al., "Dodecylbenzene transformations: Dealkylation and . . . ," Applied Catalysis A: General, v 363, n 1-2, p. 100-108, Jul. 1, 2009.

Schmidt et al., "Disproportionation of Light Paraffins," Energy and Fuels, v 22, n 3, p. 1812-1823, May/Jun. 2008.

Shi et al., "Influence of initiators on . . . ," Journal of Fuel Chemistry and Technology, v 36, n 3, p. 306-310, Jun. 2008.

Shi et al., "Isomerization of normal hexane . . . ," Ranliao Huaxue Xuebao/Journal of Fuel Chemistry and Technology, v 36, n 5, p. 594-600, Oct. 2008.

Ibragimov et al., "Isomerization of Light Alkanes . . . ," Theoretical Foundations of Chemical Engineering (2013), 47(1), 66-70.

Berenblyum et al., "The nature of catalytic activity . . . ," Applied Catalysis, A: General (2006), 315, 128-134.

Dötterl et al., "Catalytic coupling and cracking . . . ," Catalysis Communications (2012), 19, 28-30.

Vasina et al., "Effect of Adamantane-Containing Additives . . . ," Russian Journal of Physical Chemistry A (2013), 87(1), 20-22.

Liu et al., "Alkylation of isobutane/butene with . . . ," Huaxue Fanying Gongcheng Yu Gongyi (2004), 20(3), pp. 229-234.

Huang et al., "Alkylation of isobutane with butene in . . . ," Shiyou Daxue Xuebao, Ziran Kexueban (2003), 27(4), pp. 120-122.

Huang et al., "Alkylation of isobutane with butene . . . ," Shiyou Lianzhi Yu Huagong (2002), 33(11), pp. 11-13.

Liu et al., "Isobutane alkylation catalyzed by composite . . . ," Ranliao Huaxue Xuebao (2006), 34(3), pp. 328-331.

Liu et al., "Isobutane alkylation over ionic . . . ," Huaxue Fanying Gongcheng Yu Gongyi (2009), 25(4), pp. 311-317.

Liu et al., "Research progress of ionic liquids . . . ," Huaxue Shiji (2010), 32(12), pp. 1085-1088.

Liu et al., "Study on the Alkylation of . . . ," Fenzi Cuihua (2010), 24(3), pp. 217-221.

Liu et al., "Ionic liquid alkylation process . . . ," Oil & Gas Journal (2006), 104 (40), pp. 52-56.

Meyer et al., "Effective n-octane isomerization . . . ," Chemical Communications (Cambridge, United Kingdom) (2010), 46(40), pp. 7625-7627.

Shiriyazdanov et al., "Alkylation of isobutane by the butane-butene . . . ," Theoretical and Experimental Chemistry (2011), 47(1), pp. 45-48.

Shengwei et al., "Improved 1-butene/isobutane alkylation . . . ," Journal of Catalysis (2009), 268(2), pp. 243-250.

Xing et al., "Chlorogallate(III) ionic liquids: Synthesis, acidity . . . " Science China: Chemistry (2012), 55(8), pp. 1542-1547.

Xing et al., "Isobutane alkylation using acidic ionic . . . ," Catalysis Communications (2012), 26, pp. 68-71.

Yoo et al., "Ionic liquid-catalyzed alkylation of . . . ," Journal of Catalysis (2004), 222(2), pp. 511-519.

Yoo et al., "Preparation and Characterization of . . . ," AIChE Annual Meeting, Conference Proceedings, Cincinnati, OH, United States, Oct. 30-Nov. 4, 2005, 289i/1-289.

Zhang et al., "Isomerization of n-Pentane Catalyzed by . . . ," Industrial & Engineering Chemistry Research (2008), 47(21), pp. 8205-8210.

Meyer et al. "Acidic ionic liquids for n-alkane isomerization in a liquid-liquid or slurryphase reaction mode," DGMK Conference on Catalysis (2011), pp. 37-44.

* cited by examiner

US 9,096,483 B2

CATALYTIC ISOMERIZATION OF HEXANES USING IONIC LIQUIDS

This application claims priority to U.S. application Ser. No. 13,931,765, entitled "CATALYTIC ISOMERIZATION OF PARAFFINS USING IONIC LIQUIDS," filed Jun. 28, 2013.

BACKGROUND OF THE INVENTION

The Reid vapor pressure (RVP) of gasoline has been utilized by the Environmental Protection Agency as a means of regulating volatile organic compounds emissions by transportation fuels and for controlling the formation of ground level ozone. As these regulations become more stringent and as more ethanol (which has a high vapor pressure) is blended into gasoline, $C_5$ paraffins need to be removed from the gasoline pool. Moreover, the need to remove components may also extend to some $C_6$ paraffins. This may result in refiners being oversupplied with $C_5$ paraffins and possibly $C_6$ paraffins.

Disproportionation reactions offer a possible solution to this problem. The disproportionation of paraffins (e.g., isopentane ($iC_5$)) involves reacting two moles of hydrocarbon to form one mole each of two different products, one having a carbon count greater than the starting material and the other having a carbon count less than the starting material, as shown in FIG. 1. The total number of moles in the system remains the same throughout the process, but the products have different carbon counts from the reactants. Additional secondary disproportionation-type reactions can occur in which two hydrocarbons having different carbon numbers react to form two different hydrocarbons having different carbon numbers from those of the feed where the total number of carbons in the products does not change from the total number in the feed (e.g., pentane and octane reacting to form hexane and heptane).

There are a number of different catalysts that have been shown to produce the desired paraffin disproportionation reaction, including zeolites, sulfated zirconias, $AlCl_2/SiO_2$, ionic solids, platinum on chlorided $Al_2O_3/Ga_2O_3$ supports, supported ionic liquids, $Pt/W/Al_2O_3$ and $HF/TiF_4$. However, these processes have a number of disadvantages. The processes using zeolites, sulfated zirconias, $AlCl_2/SiO_2$, ionic solids, and platinum on $Al_2O_3/Ga_2O_3$ supports require elevated temperatures (e.g., 120-450° C.) to carry out the transformation. The $HF/TiF_4$ system is capable of disproportionation at 51° C., but it utilizes dangerous HF. The supported ionic liquid is active from about 85-125° C. and is composed of the Brønsted acidic trimethylammonium cation. Since the ionic liquid's organic cation is composed of this Brønsted acid, the acid concentration within this catalyst is stoichiometric with respect to the ionic liquid and quite high. Moreover, the supported ionic liquid is deactivated by leaching of the ionic liquid from the support. Additionally, the use of a support increases the cost of the catalyst and may result in a chemical reaction of the support with the acidic ionic liquid over time, as happens when $AlCl_3$ is immobilized on silica.

Isomerization processes have been used to improve the low octane numbers (RON) of light straight run naphtha. Isomerization processes involve reacting one mole of a hydrocarbon (e.g., normal pentane) to form one mole of an isomer of that specific hydrocarbon (e.g., isopentane), as shown in FIG. 2. The total number of moles remains the same throughout this process, and the product has the same number of carbons as the reactant.

Current isomerization processes use chlorided alumina, sulfated zirconia, or zeolites in conjunction with platinum. Process temperatures range from about 120° C. for chlorided alumina up to about 260° C. for zeolite type catalysts. These reactions are run at temperatures which allow the feed to reach equilibrium. At lower temperatures, the equilibrium favors the branched isomers possessing the higher octane number.

Isomerization processes utilizing ionic liquids have been developed. For example, US 2003/019767 describes an isomerization process for a paraffin hydrocarbon feed using an ionic liquid as a catalyst. The ionic liquid is formed from an N-containing heterocyclic and/or N-containing aliphatic organic cation and an inorganic anion derived from metal halides. The examples show a catalyst:hydrocarbon weight ratio of 1:1 or 1.5:1. The hydrocarbon feeds examined were normal pentane, normal heptane, normal octane, and 3-methylhexane.

US 2004/059173 teaches an isomerization process for linear and/or branched paraffin hydrocarbons. The catalyst comprises an ionic liquid. Over 25 wt. % of a cyclic hydrocarbon additive is included. The ionic liquid is formed from an N-containing heterocyclic and/or N-containing aliphatic organic cation and an inorganic anion derived from metal halides. The ionic liquid:hydrocarbon ratio in the examples is fixed at 1:1 volume ratio. Metal salt additives or Brønsted acids can be included. The feed is a mixture of $C_7$ hydrocarbons.

U.S. Pat. No. 7,053,261 discusses isomerization of linear and/or branched paraffin hydrocarbons using an ionic liquid catalyst in combination with a metal salt additive. The ionic liquid is formed from an N-containing heterocyclic and/or N-containing aliphatic organic cation and an inorganic anion derived from metal halides. The ionic liquid:hydrocarbon ratio in the examples is fixed at 1:1 volume ratio. The results of the gas chromatograph on the paraffin phase were not reported. The feed is a mixture of $C_7$ hydrocarbons.

All of these references describe isomerization of the feed; none describes disproportionation reactions. All of the references describe the use of ionic liquids having an acid concentration of at least about 3.0 M. The Brønsted acidic ionic liquid used in US Publication 2003/0109767 was [trimethylammonium][$Al_2Cl_7$], which has a molar concentration of HCl that ranges from 3.0-4.1M if the density is in the range of 1.1 to 1.5 g/mL. For US Publications 2004/0059173 and U.S. Pat. No. 7,053,261 the Brønsted acidic ionic liquid used was [trimethylammonium][$Al_{1.8}Cl_{6.4}$], which has a molar concentration of HCl that ranges from 3.3-4.5 M if the density is in the range of 1.1 to 1.5 g/mL. These estimated densities are within the ranges measured for similar ionic liquids.

None of the references indicate the composition of the product mixture; as a result, it is unclear what was actually formed in the reactions. Assuming that all of the other products were disproportionation products (which is unlikely to be correct as Ibragimov et al. teach that cracking occurs in addition to disproportionation (see below), but it sets an upper limit on the greatest possible conversion, yield, etc. for the disproportionation products). The conversion rates corrected for mass or volume were calculated as follows: using the reported iso-selectivity, the selectivity to other compounds was calculated as (100-iso-selectivity). The % conversion was determined from the reported %-iso yield and % iso-selectivity. The % conversion thus determined was used to determine the reaction rate by the following formula: volume rate=(% conversion/time (h))×(mL HC/mL IL) or as mass rate=(% conversion/time (h))×(g HC/g IL). The % conversion was then used with the computed selectivity to other compounds to set an upper limit on the yield of disproportionation products. The yield of the other compounds and yield of isomers was then calculated using the calculated selectivity to other compounds and the total yield. Since the reaction rate is dependent on the ratio of ionic liquid:hydrocarbon, the rates were corrected according to these ratios.

With respect to US 2003/0109767, the corrected conversion rates for mass were very low. For n-$C_5$, the corrected conversion rate for mass ranged was between 3.5 and 18.2. For n-$C_7$, it ranged from 2.6 to 9.3, for n-$C_8$, it was 3.3, and for 3-methylhexane, it was 4.7. For US 2005/059173, the corrected conversion rates for volume ranged from 0.6 to 47.1 for the $C_7$ mixture. For U.S. Pat. No. 7,053,261, the corrected conversion rates for volume ranged from 5.4 to 371.3 in the presence of an additional metal salt.

Isomerization is also described in "Isomerization of Light Alkanes Catalysed by Ionic Liquids: An Analysis of Process Parameters," Ibragimov et al., Theoretical Foundations of Chemical Engineering (2013), 47(1), 66-70. The desired reaction is stated to be isomerization, and the main isomerization products from n-hexane are said to isobutane, isopentane, and hexane isomers. However, isobutane and isopentane are not the isomerization products of n-hexane as isomerization has been defined above. In addition, the article discusses the fact that a significant amount of an undesirable disproportionation reaction begins to occur after about 2-3 hrs. The article indicates that the disproportionation reaction dominates when the ratio of catalyst to hydrocarbon ratio is 2:1, and that cracking and disproportionation dominate at 333K. Because cracking is occurring, the number of moles formed is increased. The optimum isomerization temperature was 303K. The maximum volume rate they obtained was 26 at their high mixing speeds (900 rpm or more) at 0.5 hr.

Some processes involve isomerization and then a cracking reaction in which one mole of a hydrocarbon forms two moles of product, each with a lower carbon number than the starting material. In FIG. 3, the products are illustrated as an alkene and an alkane. Additionally, the total number of moles increases throughout the process.

Alkylation processes involving ionic liquids are also known. In alkylation reactions, one mole of an alkane and one mole of an alkene react to form one mole of an alkane having a carbon number equal to the sum of the carbon numbers of the starting alkane and alkene, as shown in FIG. 4. In an alkylation process, the total number of moles in the system is reduced.

There is a need for improved processes for disproportionation and isomerization of hydrocarbons.

SUMMARY OF THE INVENTION

One aspect of the invention is a hydrocarbon conversion process. In one embodiment, the process includes isomerizing a hydrocarbon feed comprising normal $C_6$ alkane or branched $C_6$ alkane by contacting the hydrocarbon feed with a liquid catalyst in a reaction zone under isomerization conditions to form a product mixture comprising at least about 5 wt % branched $C_6$ alkanes if the hydrocarbon feed was the normal $C_6$ alkane or at least about 2 wt % normal $C_6$ alkanes if the hydrocarbon feed was the branched $C_6$ alkane in 1 hr based on the normal $C_6$ alkane or branched $C_6$ alkane in the hydrocarbon feed, wherein the liquid catalyst comprises an unsupported ionic liquid and a carbocation promoter comprising a haloalkane, and wherein a mass ratio of liquid catalyst to hydrocarbon feed is less than 0.75:1.

Another aspect of the invention is an isomerization reaction mixture. In one embodiment, the isomerization reaction mixture is of a liquid hydrocarbon feed comprising $C_6$ alkane or branched $C_6$ alkane and a liquid catalyst comprising an unsupported ionic liquid and a carbocation promoter comprising a haloalkane, wherein a mass ratio of the liquid catalyst to the hydrocarbon feed is less than 0.75:1, the isomerization reaction mixture comprising at least about 5 wt % branched $C_6$ alkanes if the hydrocarbon feed was the normal $C_6$ alkane or at least about 2 wt % normal $C_6$ alkanes if the hydrocarbon feed was the branched $C_6$ alkane in 1 hr based on the normal $C_6$ alkane or branched $C_6$ alkane in the hydrocarbon feed, the isomerization reaction mixture having a Reid vapor pressure in a range of about 1 to about 25 and an octane number in a range of about 50 to about 110.

DETAILED DESCRIPTION OF THE INVENTION

Figure 1:
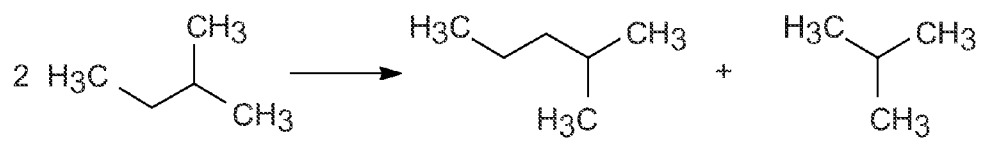
FIG. 1 illustrates the disproportionation reaction of isopentane.

A process for the disproportionation and/or isomerization of a hydrocarbon feed using a liquid catalyst comprising ionic liquids and carbocation promoters is described. The ionic liquids are unsupported and allow the reactions to occur at temperatures below about 200° C.

The disproportionation reaction involves contacting a hydrocarbon feed comprising a $C_n$ alkane with a liquid catalyst in a reaction zone to form a product mixture containing $C_{n-}$ alkanes and $C_{n+}$ alkanes, wherein the liquid catalyst comprises an unsupported ionic liquid and a carbocation promoter, and wherein n=5-12.

The isomerization reaction involves contacting the hydrocarbon feed comprising a normal $C_n$ alkane (or iso $C_n$ alkane) with a liquid catalyst in a reaction zone to form a product mixture containing iso $C_n$ alkanes (or normal $C_n$ alkanes), wherein the liquid catalyst comprises an unsupported ionic liquid and a carbocation promoter, and wherein n=5-12.

Disproportionation and isomerization occur simultaneously. There is a substantial disproportionation reaction, which can be seen by the fact that significant amounts of $C_{n+}$ and $C_{n-}$ alkanes form. The product mixture can contain at least about 3 wt % $C_{n+}$ alkanes in 1 hr based on the $C_n$ alkane fraction in the hydrocarbon feed, or at least 5 wt %, or at least about 7 wt %, or at least about 10%, or at least about 15 wt %, or at least about 20 wt %. There is a corresponding formation of the $C_{n-}$ fraction. There can be at least about 3 wt % $C_{n-}$ alkanes in 1 hr based on the $C_n$ alkane fraction in the hydrocarbon feed, or at least 5 wt %, or at least about 7 wt %, or at least about 10%, or at least about 15 wt %, or at least about 20 wt %. The percentages are based on the $C_n$ alkane fraction in the hydrocarbon feed.

It is more complex to evaluate the $C_{n+}$ and $C_{n-}$ fractions when the feed comprises more than one $C_n$ alkane. When the feed comprises more than one $C_n$ alkane, the amount of $C_{n+}$ alkane based on the highest carbon number in the feed can be used. For example if, the feed comprises $C_5$ and $C_6$, the amount of $C_{n+}$ can be evaluated using the $C_7$ fraction. When the feed comprises $C_5$ and $C_8$, the increase may be evaluated using the $C_9$ fraction.

For a feed comprising $C_5$, at least about 5 wt % each of $C_{4-}$ and $C_{6+}$ forms within 30 min, or at least about 10 wt %, or at least about 15 wt %. At least about 10 wt % each of $C_{4-}$ and $C_{6+}$ forms within 1 hr, or at least about 15 wt %, or at least about 20 wt %.

For a feed comprising $C_6$, at least about 3 wt % each of $C_{5-}$ and $C_{7+}$ forms within 30 min. At least about 5 wt % each of $C_{5-}$ and $C_{7+}$ forms within 1 hr, or at least about 6 wt %, or at least about 7 wt %.

For a feed comprising $C_7$, at least about 3 wt % each of $C_{6-}$ and $C_{8+}$ forms within 1 hr, or at least about 5 wt %, or at least about 7 wt %.

Another indication of the existence of the disproportionation reaction is that the number of moles in the product is nearly equal to the number of moles initially present.

There can also be a substantial isomerization reaction, which can be seen by the fact that significant amounts of iso $C_n$ alkanes form from normal $C_n$ alkanes, and normal $C_n$ alkanes form from iso $C_n$ alkanes initially. The product mixture can contain at least about 2 wt % normal $C_n$ alkanes in 1 hr based on the iso $C_n$ fraction in the hydrocarbon feed, or at least about 3 wt %, or at least 4 wt %, or at least 5 wt %, or at least about 7 wt %, or at least about 10 wt %. The product mixture can contain at least about 5 wt % iso $C_n$ alkanes in 1 hr based on the normal $C_n$ fraction in the hydrocarbon feed, or at least about 10 wt %, or at least about 15 wt %, or at least about 20 wt %.

For normal $C_5$ isomerization, at least about 10 wt % of iso $C_5$ forms within 30 min, or at least about 15 wt %. At least about 15 wt % iso $C_5$ forms within 1 hr, or at least about 20 wt %.

For iso $C_5$ isomerization, at least about 2 wt % of normal $C_5$ forms within 1 hr min, or at least about 3 wt %, or at least about 4 wt %, or at least about 5 wt %.

For normal $C_6$ isomerization, at least about 5 wt % of iso $C_6$ forms within 30 min, or at least about 7 wt %, or at least about 9 wt %, or at least about 10 wt %. At least about 10 wt % iso $C_6$ forms within 1 hr, or at least about 12 wt %, or at least about 13 wt %, or at least about 14 wt %.

For normal $C_7$ isomerization, at least about 5 wt % of iso $C_7$ forms within 1 hr, or at least about 10 wt %, The conversion rate for volume can be calculated as volume rate=(% conversion/time (h))×(mL HC/mL IL), where the mL of IL is determined by taking the mass of the ionic liquid and carbocation promoter and dividing by the density of the pure ionic liquid. The conversion rate for volume is at least about 60 in the absence of an added metal salt, or at least about 70, or at least about 80, or at least about 90, or at least about 100, or at least about 120, or at least about 140, or at least about 160, or at least about 180, or at least about 200, or at least about 250, or at least about 300, or at least about 350, or at least about 400, or at least about 450, or at least about 500.

The conversion rate for mass can be calculated as mass rate=(% conversion/time (h))×(g HC/g IL), where the mass of the IL is taken to be the summed mass of the IL and carbocation promoter. The conversion rate for mass in the absence of a metal salt is at least about 20, or at least about 30, or at least about 40, or at least about 50, or at least about 60, or at least about 70, or at least about 80, or at least about 90, or at least about 100, or at least about 110, or at least about 120, or at least about 130, or at least about 140, or at least about 150, or at least about 175, or at least about 200, or at least about 220 or at least about 230, or at least about 240, or at least about 250, or at least about 250.

The present invention provides a method of disproportionating a hydrocarbon feed using less ionic liquid, which is expensive, and obtaining better results at a faster rate. It also provides a method of isomerizing a hydrocarbon feed using less ionic liquid, and obtaining better results at a faster rate.

The hydrocarbon feed can be straight chain paraffins, branched chain paraffins, cycloparaffins, naphthenes, or combinations thereof. The hydrocarbon feed may contain a single $C_n$ alkane, such as pentane, or mixtures of two or more alkanes, such as pentane and hexane, or pentane, hexane, and heptane.

In some embodiments, the hydrocarbon feed can be a mixture of 2, 3, 4, 5, or 6 or more consecutive carbon numbers. Typically, there will be one, two, or three carbon numbers that form most of the feed. For example, there could be greater than about 50% of one carbon number, or greater than about 60%, or greater than about 70%, or greater than about 80%. In some embodiments, two or three carbon numbers (or more) could form greater than about 50% of the feed, or greater than about 60%, or greater than about 70%, or greater than about 80%.

In some embodiments, the $C_n$ alkane can be substantially pure $C_n$ alkane, e.g., greater than about 90% of a $C_n$ alkane, such as pentane, or greater than about 95%, or greater than about 97%, or greater than about 98%, or greater than about 99%.

In some embodiments, the $C_n$ alkane can be substantially pure normal $C_n$ alkane or substantially pure iso $C_n$ alkane, e.g., greater than about 90% of a specific normal or iso $C_n$ alkane, such as normal pentane, or greater than about 95%, or greater than about 97%, or greater than about 98%, or greater than about 99%.

In other embodiments, mixtures of normal $C_n$ alkane and iso $C_n$ alkane (both a single $C_n$ alkane, such as pentane, and two or more $C_n$ alkanes, such as pentane and hexane) are used. The ratio of normal $C_n$ alkane to iso $C_n$ alkane is typically in the range of about 90:10 to about 10:90, or about 80:20 to about 20:80, or about 70:30 to about 30:70, or about 60:40 to about 40:60, or about 50:50.

Figure 2:
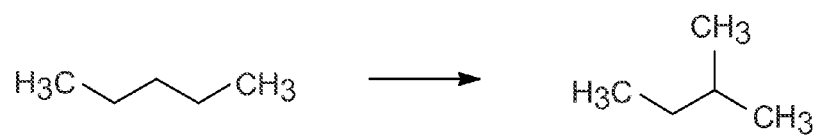
FIG. 2 illustrates the isomerization reaction of n-pentane.
Figure 3:
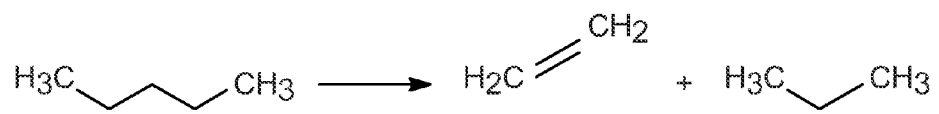
FIG. 3 illustrates a cracking reaction of n-pentane.
Figure 4:
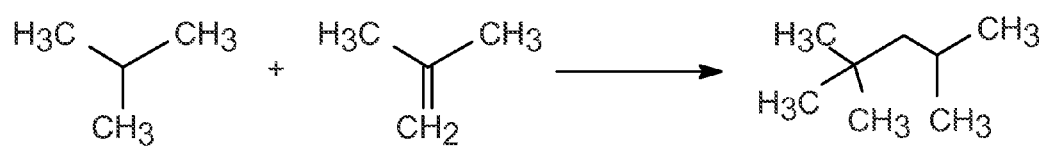
FIG. 4 illustrates an alkylation reaction of isobutane and isobutene.

As discussed above, the disproportionation reaction of a $C_n$ alkane produces $C_{n-}$ and $C_{n+}$ alkanes. For example, the disproportionation of $C_5$ produces $C_{4-}$ and $C_{6+}$ alkanes. The presence of the $C_{n+}$ fraction distinguishes the disproportionation reaction (FIG. 1) from isomerization reactions which produce isomers of the $C_n$ starting material (FIG. 2), or isomerization and cracking which produces isomers of the $C_n$ starting material and $C_{n-}$ alkanes due to cracking (FIGS. 2 and 4). The hydrocarbon feed can be dried to remove water before being contacted with the liquid catalyst. The feed can also be treated to remove undesirable reactive compounds such as alkenes, dienes, nitriles, and the like using known treatment processes.

The hydrocarbon feed can be a fluid. The fluid can be a liquid, a vapor, or a mixture of liquid and vapor. When a liquid or liquid-vapor mixture is used, the method is one of the few liquid-liquid disproportionation methods available.

The processes can produce mixtures of alkanes having desirable RVP and RON. The RVP and RON values are calculated on the $C_{5+}$ fraction. The RVP was calculated as the vapor pressure for the system when the vapor:liquid ratio is 4:1 by volume using the Peng Robinson fluid properties model. The RON was calculated with linear volumetric blending, and the RON values used for this calculation were based on the values listed in Phillips 66 Reference Data for Hydrocarbons and Petro-Sulfur Compounds, Bulletin No. 521.

In one embodiment, the product mixture of alkanes has an RVP in the range of about 1 to about 25, or about 8 to about 16, and an RON in a range of about 50 to about 110, or about 60 to about 100. In another embodiment, the product mixture of alkanes has a similar RVP and RON. The octane numbers can be increased by isomerization of the linear paraffins to the corresponding branched compounds.

In some embodiments, the RVP of the product mixture is less than the RVP of the hydrocarbon feed. In some embodiments, the RVP is reduced at least about 5 numbers compared to the hydrocarbon feed, or at least about 7 numbers, or at least about 8 numbers. For example, the RVP for pure (i.e., greater than 99%) normal pentane is 15.6, and the RVP for the product mixture made from substantially pure normal pentane is 13.0 to 13.5. The RVP for pure (i.e., greater than 99%) isopentane is 20.4, and the RVP for the product mixture made from substantially pure isopentane is 12.3 to 12.5.

When the mass ratio of branched alkanes to normal alkanes (i/n) produced from converted pentane feed is in the range of about 6:1 to about 17:1, the selectivity for isoparaffins is in the range of about 70 to about 90%, and when it is in the range of about 7:1 to about 17:1, the selectivity for isoparaffins is in the range of about 80 to about 90%. The high branched to normal ratios for alkanes obtainable with this system are notable, especially in comparison to the methods employing dehydrogenation and metathesis catalysts to effect disproportionation. Generally, when these catalysts are employed, the major isomers formed within the $C_{n-}$ and $C_{n+}$ systems are normal paraffins. The formation of large amounts of normal paraffins is typically not desired due to their low octane numbers.

The formula for calculating the i/n ratio of the product for pure alkanes is (wt. % $iC_{n-}$+×wt. % $iC_n$+wt. % $iC_{n+}$)/(wt. % $nC_{n-}$+y wt. % $nC_n$+wt. % $nC_{n+}$) with n− greater than or equal to 4, x=1 and y=0 when $C_n$=normal alkane and x=0 and y=1 when $C_n$=isoalkane. For example, for $C_5$, the calculation would be (wt. % $iC_4$+×wt. % $iC_5$+wt. % $iC_6$+wt. % $iC_7$+wt. % $iC_8$)/(wt. % $nC_4$+y wt. % $nC_5$+wt. % $nC_6$+wt. % $nC_7$+wt. % $nC_8$); where x=1 and y=0 when $C_n$=$nC_5$ and x=0 and y=1 when $C_n$ is $iC_5$). Although $C_{9+}$ alkanes will be present in small amounts, they should not substantially affect the i/n ratio as reported. In addition, the $C_{3-}$ compounds are not included because they don't have normal and iso isomers.

The lower reactivity of normal pentane ($nC_5$) has made it generally difficult to for the development of a commercial process using $nC_5$. However, disproportionation of $nC_5$ at reasonable rates has been demonstrated in more than one embodiment of the present invention.

In order for these reactions to proceed, a stable carbocation likely needs to be present. Carbocations readily undergo skeletal rearrangement at low temperatures. Even at −90° C., rapid rearrangement is observed for degenerate 1,2-methide shifts. Frequently, carbocations are transient intermediates and are short-lived. However, persistent carbocations have been observed in superacidic media.

Ionic liquids offer a number of unique features which make them particularly well suited as reaction mediums for low temperature disproportionation and isomerization. These features include: (1) extremely low volatility, resulting in little to no solvent loss, (2) high chemical diversity, allowing for specific properties to be readily incorporated into the solvent, (3) good thermal stability, (4) readily recyclable, (5) wide liquid ranges, and (6) in some cases (e.g., 1-ethyl-3-methylimidazolium chloroaluminates), they have been shown to be superacidic.

The liquid hydrocarbon feed comprises a $C_n$ alkane where n=5-12. A normal $C_n$ alkane is converted to a product mixture comprising iso $C_n$ hydrocarbons, normal and iso $C_{n-}$ hydrocarbons and normal and iso $C_{n+}$ hydrocarbons, and an iso $C_n$ alkane is converted to a product mixture comprising normal $C_n$ hydrocarbons, normal and iso $C_{n-}$ hydrocarbons and normal and iso $C_{n+}$ hydrocarbons. A blend of normal and iso $C_n$ alkane is converted to a product mixture comprising normal and iso $C_n$ hydrocarbons, normal and iso $C_{n-}$ hydrocarbons and normal and iso $C_{n+}$ hydrocarbons, and the highest concentration of $C_{n+}$ hydrocarbons is the $C_{n+1}$ hydrocarbon. For example, for a feed of n-pentane, the product mixture would be isopentane, $C_{4-}$ hydrocarbons and $C_{6+}$ hydrocarbons, and for a feed of isopentane, the product mixture would be n-pentane, $C_{4-}$ hydrocarbons and $C_{6+}$ hydrocarbons, with the highest concentration being $C_6$ hydrocarbons for the $C_{n+}$ fractions. A feed comprising a blend of n-pentane and isopentane would produce a product mixture of n-pentane and isopentane, $C_{4-}$ hydrocarbons and $C_{6+}$ hydrocarbons. The process is particularly useful for conversion of $C_5$, $C_6$, and $C_7$ alkanes.

The liquid catalyst comprises an ionic liquid and a carbocation promoter. The ionic liquid is in liquid form; unlike prior art processes, it is not supported on an oxide support. In addition, the ionic liquids employed herein do not contain cations which are Brønsted acids, so the acid concentration within these systems is less than prior art processes using ionic liquids which are Brønsted acidic organic cations. The acid concentration is less than about 2.5 M, or less than about 2.25 M, or less than about 2.0 M, or less than about 1.75 M, or less than about 1.5 M.

One or more ionic liquids can be used.

The ionic liquid comprises an organic cation and an anion. Suitable organic cations include, but are not limited to:

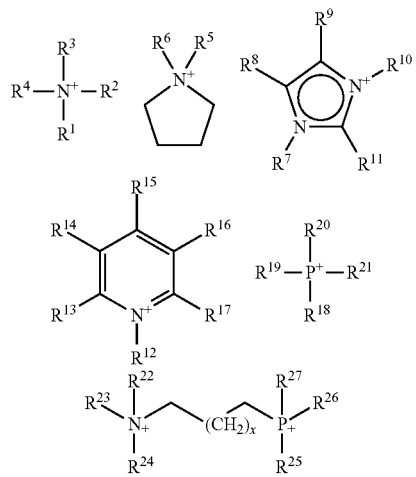

where $R^1$-$R^{27}$ are independently selected from $C_1$-$C_{20}$ hydrocarbons, $C_1$-$C_{20}$ hydrocarbon derivatives, halogens, and H, and x=1-4, or combinations thereof. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, sulfates, bisulfates, nitrates, sulfonates, fluoroalkanesulfonates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$, or combinations thereof.

The ionic liquid is combined with one or more carbocation promoters. In some embodiments, the carbocation promoter is added to the ionic liquid. In other embodiments, the carbocation promoter is generated in situ. However, in situ production might not provide reproducible results.

Suitable carbocation promoters include, but are not limited to, halo-alkanes, mineral acids alone or combined with alkenes, and combinations thereof. Suitable halo-alkanes include but are not limited to 2-chloro-2-methylpropane, 2-chloropropane, 2-chlorobutane, 2-chloro-2-methylbutane, 2-chloropentane, 1-chlorohexane, 3-chloro-3-methylpentane, or combinations thereof. In some embodiments, the carbocation promoters are not cyclic alkanes.

Suitable mineral acids include, but are not limited to, HCl, HBr, $H_2SO_4$, and $HNO_3$. Although HF can also be used, it is less desirable due to safety issues. If the mineral acid is not strong enough to protonate off a hydrogen from a C—H bond, isobutene or another alkene can be added with the mineral acid to produce the desired carbocation promoter. The mineral acid can be generated in situ by the addition of a compound that reacts with the ionic liquid. In situ acid generation can also occur as a result of reaction with water present in the system. The mineral acid may also be present as an impurity in the ionic liquid.

2-chloropropane, and 2-chlorobutane were used successfully as carbocation promoters. HCl was generated in situ by the addition of methanol to the ionic liquid, resulting in the partial degradation of the $Al_2Cl_7^-$ anion with concomitant formation of HCl. This method was sufficient to catalyze the disproportionation.

The molar ratio of the carbocation promoter to the ionic liquid in the liquid catalyst is typically in the range of about 0:1 to about 3:1, or about 0.1:1 to about 1:1. This relates to forming the carbocation promoter from the halo-alkane or mineral acid. This ratio is important relative to the specific type of anion. For example, if the anion is $AlCl_4^-$, a reaction is unlikely to occur or will be poor because the aluminum is fully coordinated. However, if the anion is $Al_2Cl_7^-$, there is some aluminum present that can coordinate to the carbocation promoter's anion, assisting in generating the carbocation from the carbocation promoter.

The mass or volume ratios of liquid catalyst (ionic liquid and carbocation promoter) to hydrocarbon feed are less than 1:1. This is desirable because the ionic liquid is an expensive component in the process. In some embodiments, the mass ratio of ionic liquid to hydrocarbon feed is not more than about 0.75:1, or not more than about 0.7:1, or not more than about 0.65:1, or not more than about 0.60:1, or not more than about 0.55:1, or not more than about 0.50:1. In some embodiments, the volume ratio of ionic liquid to hydrocarbon feed is not more than about 0.8:1, or not more than about 0.7:1, or not more than about 0.6:1, or not more than about 0.5:1, or not more than about 0.45:1, or not more than about 0.4:1, or not more than about 0.35:1, or not more than about 0.3:1, or not more than about 0.25:1.

The liquid hydrocarbon feed is contacted with the liquid catalyst at temperatures up to the decomposition temperature of the ionic liquid, typically of about 250° C. or less, or of about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 250° C., or about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 8.1 MPa. The pressure should be sufficient to ensure that the hydrocarbon feed is in a liquid state. Small amounts of vapor may also be present, but this should be minimized. The reaction typically takes places in the presence of a gas. Suitable gases include, but are not limited to nitrogen, hydrogen, argon, helium, hydrogen chloride and the like.

The residence time in the reaction zone is generally less than about 10 hr, or less than 7 hr, or less than 5 hr, or less than 4 hr, or less than 3 hr, or less than 2 hr, or less than 1 hr. The reaction time and conversion are based on the time needed to reach equilibrium of the initial reaction products, such as 2-methylpentane and isobutane from the disproportionation of isopentane. The reaction time is a function of the degree of mixing, the reaction temperature, the concentration of the carbocation promoter, the molar ratio of the carbocation promoter to ionic liquid, and the mass/volume ratio of ionic liquid to hydrocarbon being reacted. Generally, increasing any of these conditions will increase the reaction rate. Under some conditions, greater than 90% conversion is possible.

The % selectivity for the disproportionation reaction is defined as: [(sum of the wt. % $C_{n-}$ and $C_{n+}$ compounds)/(100-wt. % $C_n$ feed)]×100. The % selectivity for the disproportionation reaction is typically at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 94%.

For blends, the selectivity for the disproportionation reaction would be similar as above. For example, for a blend consisting of 50% isopentane and 50% n-pentane, the % selectivity for the disproportionation reaction is defined as: [(sum of the wt. % $C_{4-}$ and $C_{6+}$ compounds)/(100-wt. % $C_n$ feed)]×100, where the $C_n$ feed is taken to be the summed wt. % of isopentane and n-pentane. A simple equation similar to this may not be adequate for more complex blends.

The % selectivity for the isomerization reaction to isoparaffins ($S_{iso-isom}$) is defined as (z(wt. % isoparaffin $C_n$))/(100–wt. % $C_n$ feed)×100, where z=0 when the $C_n$ feed is isoparaffin and z=1 when the $C_n$ feed is n-paraffin. The % selectivity for isoparaffin disproportionation is defined as (wt. % isoparaffins of $C_{n-}$+wt. % isoparaffins $C_{n+}$)/(100–wt. % $C_n$ feed)×100 ($S_{iso-disp}$). The % selectivity for isoparaffins is defined as (wt. % isoparaffins of $C_{n-}$+wt. % isoparaffins $C_{n+}$+z(wt. % isoparaffin $C_n$))/(100–wt. % $C_n$ feed)×100, where z=0 when the $C_n$ feed is isoparaffin and z=1 when the $C_n$ feed is n-paraffin ($S_{isoparaffin}$); or $S_{isoparaffin} = S_{iso-isom} + S_{iso-disp}$. The selectivity for isoparaffins is typically at least about 40%, or at least about 45%, or at least about 50%, or at least about 55%, or at least about 60%, or at least about 65%, or at least about 70%, or at least about 75%, or at least about 80%, or at least about 85%, or at least about 90%.

For blends, the selectivity for isoparaffins would be similar as above. For example, for a blend consisting of 50% isopentane and 50% n-pentane, the % selectivity for the isoparaffins reaction is defined as: [(sum of the wt. % $iC_4$ and $iC_{6+}$ compounds)/(100–wt. % $C_n$ feed)]×100, where the $C_n$ feed is taken to be the summed wt. % of isopentane and n-pentane. A simple equation similar to this may not be adequate for more complex blends.

The selectivity is highly dependent on the type of feed used. For example, for $iC_5$, the selectivity for the disproportionation reaction typically can be in the range of about 92-94%. However, the selectivity for the disproportionation reaction for $nC_5$ is much lower, e.g., in the range of about 67-76% because a substantial amount of isomerization to isopentane occurs.

Conversion for the disproportionation and isomerization reactions is defined as 100−wt. % $C_n$ feed. The conversion is typically at least about 50%, or at least about 55%, or at least about 60%, or at least about 65%, or at least about 70%, or at least about 75%, or at least about 80%, or at least about 85%, or at least about 90%.

For blends, the conversion would be the same as above. For example, for a blend consisting of 50% isopentane and 50% n-pentane, the % conversion is equal to 100−wt. % $C_n$ feed, where the $C_n$ feed taken to be the summed wt. % of isopentane and n-pentane.

For example, with an $iC_5$ feed, initially the products are primarily the isoparaffins of the $C_4$ and $C_6$ compounds along with some $nC_5$. Because $iC_5$ is more thermodynamically preferred, the amount of $nC_5$ that forms is relatively small, and the dominating pathway is disproportionation. Since the kinetic products are isoparaffins, the selectivity for isoparaffins can be similar to disproportionation. However, the mixture is not completely at equilibrium, so as the product continues to react, some of the initially formed isoparaffins of the disproportionation products begin to convert to their corresponding n-paraffins. As this occurs, the selectivity for isoparaffins decreases, but the selectivity for disproportionation does not.

With a feed of $nC_5$, the initial products are again primarily the isoparaffins of the $C_4$ and $C_6$ compounds and $iC_5$. Because $nC_5$ is thermodynamically disfavored, the amount of $iC_5$ that forms is substantially greater relative to the formation of $nC_5$ from the $iC_5$ feed. In this case, significant amounts of $nC_5$ are converted to $iC_5$. Since the initial products are isoparaffins, the selectivity for isoparaffins remains high. However, since a significant portion of $nC_5$ is converted to $iC_5$, the selectivity for disproportionation is less than it was when $iC_5$ is used. As the reaction progresses, $iC_5$ and $nC_5$ continue to disproportionate and the selectivity for disproportionation increases during the reaction. Conversely, the selectivity for isoparaffins decreases as the mixture equilibrates because the initially formed isoparaffin disproportionation products convert to their normal isomers.

At higher temperatures, the relative concentration of normal paraffins increases, which ultimately results in decreased selectivities for isoparaffins relative to lower temperatures.

Although the reaction will proceed simply by contacting the hydrocarbon feed and the liquid catalyst, the reaction rate is generally too slow to be commercially viable. The reaction rate can be substantially increased by increasing the stirring speed of the reaction. This indicates that under some conditions the rate of reaction is mass transfer limited and is not reflective of the true elementary steps of the reaction. In addition to simply stirring the reaction mixture, a baffle can be included in the reactor to aid in obtaining good mixing. The baffle helps to prevent a vortex from forming in the reactor. The formation of a vortex would reduce the amount of mixing even in the presence of stirring.

Figure 5:
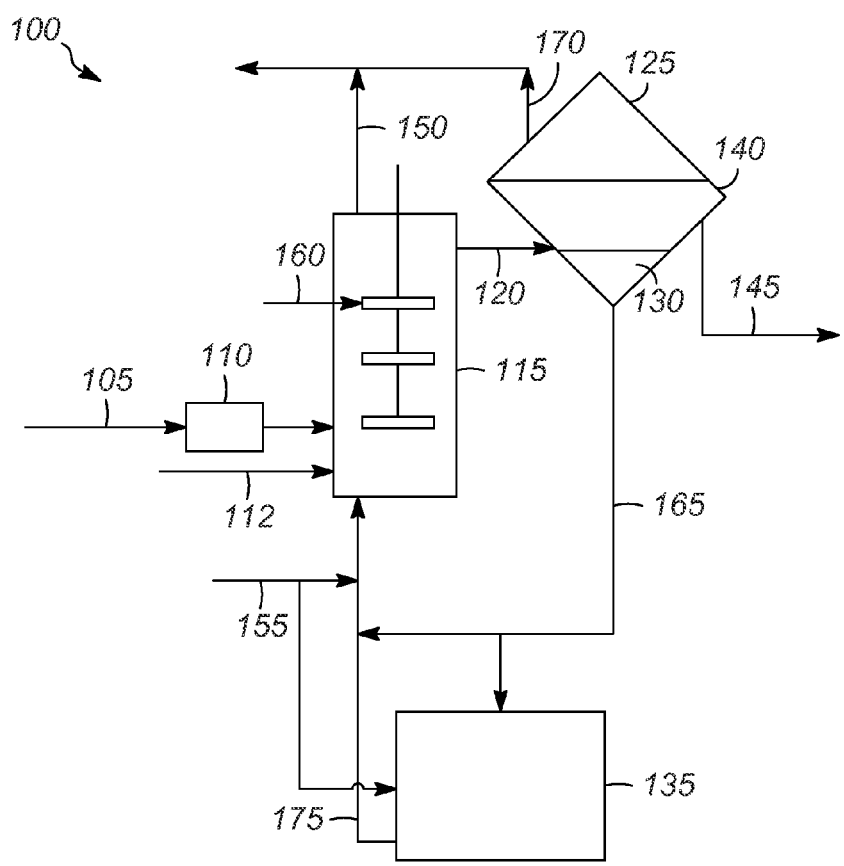
FIG. 5 is a schematic of one embodiment of the process of present invention.

One embodiment of the process 100 is a continuous-flow reactor as shown in FIG. 5. Feed 105, including the liquid hydrocarbon and carbocation promoter (if present), passes over a drying bed 110 and is continuously introduced to the reactor 115 while simultaneously withdrawing product 120. The liquid catalyst (or ionic liquid alone) 112 is introduced to the reactor 115. The carbocation promoter can be added with the hydrocarbon feed, or with the ionic liquid, or both. The reactor desirably includes a stirrer 160 to mix the hydrocarbon feed 105 and the liquid catalyst. The gaseous products 150 can be separated in the reactor 115. The effluent 120 is sent to a settler 125, where the heavier ionic liquid phase separates as a bottom layer 130. The used ionic liquid stream 165 can be recycled to the reactor 115 and/or the regenerator 135. The upper hydrocarbon layer phase 140 is removed from the settler 125, yielding the liquid product 145. The gaseous products 170 are separated in settler 125. These gaseous products 170 can be combined with gaseous products 150 which could then be used as feed in alkylation units (not shown). The used ionic liquid 165 can be regenerated in regenerator 135 to remove deactivated liquid catalyst so it can be reused. Fresh ionic liquid 155 can be added to the regenerated ionic liquid stream 175 as needed and sent to the reactor 115. Fresh ionic liquid can also be added to the regenerator 135, as needed.

The ionic liquid can be regenerated in a variety of ways. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. No. 7,651,970; U.S. Pat. No. 7,825,055; U.S. Pat. No. 7,956,002; U.S. Pat. No. 7,732,363, each of which is incorporated herein by reference. Another method involves contacting the ionic liquid containing the conjunct polymer with a reducing metal (e.g., Al) in the presence of an inert hydrocarbon (e.g. hexane) and heating to about 100° C. The conjunct polymer will be transferred to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the conjunct polymer to be removed from the IL phase. See e.g., U.S. Pat. No. 7,727,925, which is incorporated herein by reference. The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740, which is incorporated herein by reference. The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771, which is incorporated herein by reference. Still another method involves adding a suitable substrate (e.g. pyridine) to the ionic liquid containing the conjunct polymer. After a period of time, an inert hydrocarbon would be added to wash away the liberated conjunct polymer. The ionic liquid precursor [butylpyridinium][Cl] would be added to the ionic liquid (e.g. [butylpyridinium][Al$_2$Cl$_7$]) containing the conjunct polymer followed by an inert hydrocarbon. After a given time of mixing, the hydrocarbon layer would be separated, resulting in a regenerated ionic liquid. See, e.g., U.S. Pat. No. 7,737,067, which is incorporated herein by reference. Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623, which is incorporated herein by reference.

In some embodiments, unreacted carbocation promoter is separated from the product mixture and recovered. It can be recycled and used the reaction. Alternatively, it could be used in other processes.

The contacting step may be practiced in laboratory scale experiments through full scale commercial operations. The process may be operated in batch, continuous, or semi-continuous mode. The contacting step can take place in various ways, with both countercurrent and co-current flow processes being suitable. The order of addition of the reactants is not critical. For example, the reactants can be added individually, or some reactants may be combined or mixed before being combined or mixed with other reactants.

Disproportionation of nC$_5$ and iC$_5$ has also been achieved at temperatures as low as 45° C. The reaction was faster with iC$_5$ than with nC$_5$. Gas chromatograph (GC) analysis revealed that the primary compounds formed were isoparaffins using the analytical method ASTM UOP690-99; very few C$_{3-}$ hydrocarbons formed. The products of the reaction for n-C$_5$ were broadly divided into the following categories: C$_{3-}$, n-C$_4$, iC$_4$, iC$_5$, C$_6$ paraffins (C$_6$P) and C$_{7+}$ hydrocarbons. The products of the reaction for iso C$_5$ were broadly divided into the following categories: C$_{3-}$, n-C$_4$, iC$_4$, nC$_5$, C$_6$ paraffins (C$_6$P) and C$_{7+}$ hydrocarbons. The selectivity to these products was constant over a wide range of isopentane conversions. However, at higher conversions, the selectivity to C$_6$ paraffins decreased, while the selectivity to iC$_4$ and C$_{7+}$ hydrocarbons increased, which is likely the result of secondary disproportionation-type reactions. An analysis of both the headspace and the liquid phase revealed that C$_{3-}$ hydrocarbons form in small amounts.

In some places, demand for iC$_4$ exceeds supply, and disproportionation could help alleviate this problem.

For iso-pentane conversion, the selectivity to the various products (product selectivity being defined as [wt. % compound/(100-wt. % C$_n$ feed)]*100) was nearly constant up to about 52% conversion at 55° C. Higher isopentane conversions resulted in decreased selectivity to C$_6$ paraffins and higher selectivities to iC$_4$ and C$_{7+}$ hydrocarbons, which was likely the result of secondary disproportionation-type reactions.

With iso-pentane conversion, the extent of isomerization to n-pentane was minimal, but observable, because the reactant was already present in the more thermodynamically favored state. It was consistently observed that the selectivity for isomerization of isopentane to n-pentane centered around 7%, regardless of the % conversion of isopentane.

A significant stir rate dependence on the reaction rate was observed. Under the conditions used, the benefits of increased mixing began to taper off at stir rates greater than 700 rpm, which indicates that much of the kinetics of the reaction below 700 rpm is mass transfer limited.

The other products that form during the disproportionation reaction of isopentane were mainly isobutane and C$_{6+}$ isoparaffins. The selectivity to these products was also nearly constant with isopentane conversion. However, at higher conversions, the selectivity to the C$_6$ paraffins decreased, while there was a concomitant increase in selectivity for isobutane and C$_{7+}$ isoparaffins. It is important to note that very little C$_{3-}$ formed in the reactions at 55° C. as revealed by a headspace analysis and by the analytical method ASTM UOP980-07.

Under similar conditions (e.g., volume of ionic liquid, temperature, stir rate, etc.), the rate of nC$_5$ conversion is dependent on the type of ionic liquid used, as the same reaction proceeds at a much greater conversion rate in [1-butyl-1-methylpyrrolidinium][Al$_2$Cl$_7$] than in [tributyl(hexyl)phosphonium][Al$_2$Cl$_6$Br] ([("Bu)$_3$P(Hex)][Al$_2$Cl$_6$Br]). Despite the increase in reactivity, the selectivities for the products were similar to what was observed with the ionic liquid [("Bu)$_3$P(Hex)][Al$_2$Cl$_6$Br].

Isomerization and disproportionation of n-hexane has been found to occur at temperatures as low as 45° C. in several different ionic liquids (e.g., [("Bu)$_3$P(Hex)][Al$_2$Cl$_6$Br], [1-butyl-1-methylpyrrolidinium][Al$_2$Cl$_7$], [1-butyl-3-methylimidazolium][Al$_2$Cl$_7$] and trihexyl(tetradecyl)phosphonium heptachloroaluminate ([(n-Hex)$_3$P(tetradecyl)][Al$_2$Cl$_7$])). The promoter used in all of these reactions, except for [1-butyl-3-methylimidazolium][Al$_2$Cl$_7$], was 2-chloro-2-methylpropane, which served to generate the active tert-butyl cation. Trace amounts of water or HCl present in [1-butyl-3-methylimidazolium][Al$_2$Cl$_7$] was sufficient for the catalysis to occur. A wide range of compounds were formed, including naphthenes, n-paraffins, isoparaffins and even some aromatic complexes, but the major products are paraffins.

Increasing the concentration of 2-chloro-2-methylpropane increased the conversion, and the yield for the higher and lighter molecular weight complexes. The major light components formed were identified by headspace analysis as iC$_4$, iC$_5$, 2-methylpentane and unreacted nC$_6$. However, it did little to change the selectivity for isomerization. Similarly, increasing the reaction time, temperature, and ratio of mass of ionic liquid to mass of hydrocarbon feed increased the overall conversion. It is desirable to minimize the amount of ionic liquid used due to the cost and potential increase in the amount of feed processed per unit ionic liquid.

By the term "about," we mean within 10% of the value, or within 5%, or within 1%.

EXAMPLES

Example 1

Experimental Set Up

The set-up included a 300 mL autoclave equipped with a mechanical stirrer, pressure gauge, thermocouple, dipleg, rupture disc and valves to introduce the feed and withdraw an aliquot of hydrocarbon feed or product for GC analysis. The rupture disc vented to a knock out pot. The house nitrogen passed through a pressure regulator to a high surface sodium column and was then split: feeding to the charger for feed introduction or to a line for various uses (i.e., 2-methyl-2-chloropropane/C$_5$P introduction). The dipleg was constructed such that the height positions it in the paraffin layer. Upon opening the valve, the withdrawn paraffin layer passed through a column of silica, to the GC valve and then through a metering valve into a waste container. The reaction mixture was analyzed using the ASTM UOP690-99 method. The $S_{isoparaffin}$ was calculated by summing the wt. % contribution of the $C_4$-$C_8$ isoparaffins that are separable using the ASTM UOP690-99 method, but does not include the contributions from the $C_{9+}$ fraction. Consequently, these values represent lower limits for the selectivity. Similarly, the $S_{iso\text{-}disp}$ were determined using this analytical method and is also a lower limit. The RVP was calculated on the $C_{5+}$ fraction as the vapor pressure for the system when the vapor:liquid ratio is 4:1 by volume using the Peng Robinson fluid properties model. The RON was calculated on the $C_{5+}$ fraction with linear volumetric blending and the RON values used for this calculation were based on the values listed in Phillips 66 Reference Data for Hydrocarbons and Petro-Sulfur Compounds, Bulletin No. 521.

Example 2

Synthesis of [("Bu)$_3$P(Hex)][Al$_2$Cl$_6$Br]

An oven-dried round bottom flask was charged with [("Bu)$_3$P(Hex)][Br]. The material was attached to a rotary evaporator and dried under vacuum at 110° C. for at least 14 h. The dried [("Bu)$_3$P(Hex)][Br] was immediately brought into a nitrogen glovebox and stored there. A synthesis was achieved by massing 17.589 g (47.88 mmol) of [("Bu)$_3$P (Hex)][Br] into an oven-dried flask equipped with a stir bar in the nitrogen glovebox. To this was added 12.775 g (95.81 mmol) of AlCl$_3$ at ambient temperature. The mixture was stirred and the solids slowly reacted over the course of one week to produce a homogenous pale-yellow liquid.

Example 3

Synthesis of [1-butyl-1-methylpyrrolidinium] [Al$_2$Cl$_7$]

An oven-dried round bottom flask was charged with [1-butyl-1-methylpyrrolidinium][Cl]. The material was attached to a rotary evaporator, dried under vacuum at 110° C. for at least 14 h, and then sealed under vacuum with a connecting adapter. The dried [1-butyl-1-methylpyrrolidinium][Cl] was immediately brought into a nitrogen glovebox and stored there. A synthesis was achieved by massing 57.14 g (322 mmol) of [1-butyl-1-methylpyrrolidinium][Cl] into an oven-dried flask equipped with a stir bar in the nitrogen glovebox. To this was added 83.93 g (629 mmol) of AlCl$_3$ at ambient temperature and the mixture stirred. The solids reacted to produce a homogenous liquid.

Example 4

Synthesis of with [1-butyl-3-methylimidazolium] [Al$_2$Cl$_7$]

An oven-dried round bottom flask was charged with 1-butyl-3-methylimidazolium chloride. The material was attached to a rotary evaporator, dried under vacuum at 110° C. for at least 14 h and then sealed under vacuum with a connecting adapter. Afterwards, the dried 1-butyl-3-methylimidazolium chloride was stored in a nitrogen glovebox. A synthesis was achieved by massing 50.04 g (286 mmol) of 1-butyl-3-methylimidazolium chloride into an oven-dried flask equipped with a stir bar in the nitrogen glovebox. To this was added 76.40 g (573 mmol) of AlCl$_3$ at ambient temperature, and the mixture stirred. The solids react to produce a homogenous liquid.

Example 5 iC$_5$—Stir Rate Effect at 350 rpm with [("Bu)$_3$P (Hex)][Al$_2$Cl$_6$Br]

A 300 mL stainless steel autoclave, stainless steel baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.39 g of [("Bu)$_3$P(Hex)][Al$_2$Cl$_6$Br], and the autoclave head was attached. To the sample cylinder, 1.451 g of 2-chloro-2-methylpropane, which had previously been dried over activated sieves, was added. The sample cylinder was closed under nitrogen, and both the autoclave and sample cylinder were removed from the glovebox. The autoclave was charged with 119 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 18 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 145 psi (1 MPa), and the autoclave was then set to stir at 350 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to iso-pentane was 0.38 and the volume ratio was 0.19. The mass rate of reaction was 38, and the volume rate was 75 after 1.4 h. The results of the run are shown in Tables 1 and 2.

TABLE 1

Disproportionation and Isomerization of iso-Pentane at 55° C., 350 rpm, wt. % of reaction mixture

| t (h) | % Conv. | C3− | iC4 | nC4 | iC5 | nC5 | C6P | C7+ | i/n | S. Disp. | $S_{isoparaffin}$ |
|---|---|---|---|---|---|---|---|---|---|---|---|
| 1.4 | 20 | 0.00 | 7.20 | 0.02 | 80.46 | 1.31 | 6.84 | 4.13 | 11.2 | 93 | 82 |
| 2.7 | 28 | 0.01 | 10.38 | 0.04 | 72.48 | 2.04 | 9.93 | 5.09 | 9.94 | 92 | 84 |
| 4.4 | 36 | 0.01 | 13.64 | 0.07 | 64.29 | 2.70 | 12.75 | 6.54 | 9.48 | 92 | 85 |

TABLE 2

| Time (h) | 1.4 | 2.7 | 4.4 | NA |
|---|---|---|---|---|
| Wt. % | | | | feed |
| C3P | 0.00 | 0.01 | 0.01 | 0.00 |
| C4P | 7.22 | 10.43 | 13.71 | 0.00 |
| C5P | 81.77 | 74.53 | 66.99 | 99.86 |
| C6P | 6.84 | 9.94 | 12.74 | 0.00 |
| C7P | 1.67 | 2.47 | 3.32 | 0.00 |
| C8P | 0.52 | 0.73 | 1.00 | 0.00 |
| C9+ | 1.56 | 1.51 | 1.80 | 0.00 |
| C5N | 0.00 | 0.00 | 0.00 | 0.00 |
| C6N | 0.00 | 0.00 | 0.00 | 0.00 |
| C7N | 0.01 | 0.00 | 0.00 | 0.00 |
| C8N | 0.34 | 0.34 | 0.38 | 0.00 |
| C6A | 0.00 | 0.00 | 0.00 | 0.00 |
| C7A | 0.00 | 0.00 | 0.00 | 0.00 |
| C8A | 0.05 | 0.05 | 0.05 | 0.00 |
| nC4-nC5 unknowns | 0.00 | 0.00 | 0.00 | 0.14 |
| mmoles (based on wt. %) | | | | |
| C3P | 0 | 0 | 0 | 0 |
| C4P | 124 | 179 | 236 | 0 |
| C5P | 1133 | 1033 | 928 | 1384 |
| C6P | 79 | 115 | 148 | 0 |
| C7P | 17 | 25 | 33 | 0 |
| C8P | 5 | 6 | 9 | 0 |
| C9+ | 12 | 12 | 14 | 0 |
| C5N | 0 | 0 | 0 | 0 |
| C6N | 0 | 0 | 0 | 0 |
| C7N | 0 | 0 | 0 | 0 |
| C8N | 3 | 3 | 3 | 0 |
| C6A | 0 | 0 | 0 | 0 |
| C7A | 0 | 0 | 0 | 0 |
| C8A | 0 | 0 | 1 | 0 |
| nC4-nC5 unknowns | 0 | 0 | 0 | 2 |
| Total mmoles | 1374 | 1374 | 1372 | 1386 |

Example 6 iC5—Stir Rate Effect at 700 rpm with [("Bu)$_3$P(Hex)][Al$_2$Cl$_6$Br]

A 300 mL stainless steel autoclave, stainless steel baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.352 g of [("Bu)$_3$P(Hex)][Al$_2$Cl$_6$Br], and the autoclave head was attached. To the sample cylinder, 1.453 g of 2-chloro-2-methylpropane, which had previously been dried over activated sieves, was added. The sample cylinder was closed under nitrogen, and both the autoclave and sample cylinder were removed from the glovebox. The autoclave was charged with 112 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 15 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 115 psi (0.793 MPa), and the autoclave was then set to stir at 700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to iso-pentane was 0.40 and the volume ratio was 0.20. The mass rate of reaction was 47, and the volume rate was 93 after 1.5 h. The results of the run are shown in Tables 3 and 4.

TABLE 3

Disproportionation and Isomerization of iso-Pentane at 55° C., 700 rpm, wt. % of reaction mixture

| t (h) | % Conv. | C3– | iC4 | nC4 | iC5 | nC5 | C6P | C7+ | i/n | S. Disp. | $S_{isoparaffin}$ |
|---|---|---|---|---|---|---|---|---|---|---|---|
| 1.5 | 28 | 0.02 | 10.35 | 0.04 | 72.07 | 1.94 | 9.83 | 5.74 | 10.5 | 93 | 83 |
| 2.7 | 39 | 0.02 | 14.84 | 0.10 | 61.22 | 2.82 | 13.35 | 7.65 | 9.5 | 93 | 84 |
| 4.4 | 52 | 0.03 | 20.18 | 0.18 | 47.98 | 3.66 | 16.71 | 11.25 | 9.1 | 93 | 84 |

TABLE 4

| Time (h) | 1.5 | 2.7 | 4.4 | NA |
|---|---|---|---|---|
| Wt. % | | | | feed |
| C3P | 0.02 | 0.02 | 0.03 | 0.00 |
| C4P | 10.39 | 14.93 | 20.35 | 0.00 |
| C5P | 74.02 | 64.05 | 51.64 | 99.86 |
| C6P | 9.83 | 13.34 | 16.71 | 0.00 |
| C7P | 2.55 | 3.79 | 5.53 | 0.00 |
| C8P | 0.82 | 1.25 | 1.99 | 0.00 |
| C9+ | 1.99 | 2.17 | 3.13 | 0.00 |
| C5N | 0.00 | 0.00 | 0.00 | 0.00 |
| C6N | 0.00 | 0.00 | 0.00 | 0.00 |
| C7N | 0.00 | 0.01 | 0.01 | 0.00 |
| C8N | 0.33 | 0.37 | 0.51 | 0.00 |
| C6A | 0.00 | 0.00 | 0.00 | 0.00 |
| C7A | 0.00 | 0.00 | 0.01 | 0.00 |
| C8A | 0.06 | 0.06 | 0.09 | 0.00 |
| nC4-nC5 unknowns | 0.00 | 0.00 | 0.00 | 0.14 |
| mmoles (based on wt. %) | | | | |
| C3P | 0 | 0 | 1 | 0 |
| C4P | 179 | 257 | 350 | 0 |

TABLE 4-continued

| Time (h) | 1.5 | 2.7 | 4.4 | NA |
|---|---|---|---|---|
| C5P | 1026 | 888 | 716 | 1384 |
| C6P | 114 | 155 | 194 | 0 |
| C7P | 25 | 38 | 55 | 0 |
| C8P | 7 | 11 | 17 | 0 |
| C9+ | 16 | 17 | 24 | 0 |
| C5N | 0 | 0 | 0 | 0 |
| C6N | 0 | 0 | 0 | 0 |
| C7N | 0 | 0 | 0 | 0 |
| C8N | 3 | 3 | 5 | 0 |
| C6A | 0 | 0 | 0 | 0 |
| C7A | 0 | 0 | 0 | 0 |
| C8A | 1 | 1 | 1 | 0 |
| nC4-nC5 unknowns | 0 | 0 | 0 | 2 |
| Total mmoles | 1371 | 1370 | 1363 | 1386 |

Example 7 iC5—Stir Rate Effect at 1700 rpm with [("Bu)$_3$P(Hex)][Al$_2$Cl$_6$Br]

A 300 mL stainless steel autoclave, stainless steel baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.398 g of [("Bu)$_3$P(Hex)][Al$_2$Cl$_6$Br], and the autoclave head was attached. To the sample cylinder 1.453 g of 2-chloro-2-methylpropane, which had previously been dried over activated sieves, was added. The sample cylinder was closed under nitrogen, and both the autoclave and sample cylinder were removed from the glovebox. The autoclave was charged with 106 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 23 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 139 psi (0.958 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to iso-pentane was 0.40 and the volume ratio was 0.20. The mass rate of reaction was 41, and the volume rate was 82 after 2.5 h. The results of the run are shown in Tables 5 and 6.

TABLE 5

Disproportionation and Isomerization of iso-Pentane at 55° C., 1700 rpm, wt. % of reaction mixture

| t (h) | % Conv. | C3- | iC4 | nC4 | iC5 | nC5 | C6P | C7+ | i/n | S. Disp. | $S_{isoparaffin}$ |
|---|---|---|---|---|---|---|---|---|---|---|---|
| 2.5 | 41 | 0.01 | 15.70 | 0.13 | 58.64 | 2.94 | 14.48 | 8.09 | 9.6 | 93 | 84 |
| 3.7 | 49 | 0.02 | 19.55 | 0.19 | 50.66 | 3.51 | 16.73 | 9.34 | 9.3 | 93 | 85 |

TABLE 6

| Time (h) | 2.5 | 3.7 | NA |
|---|---|---|---|
| Wt. % | | | feed |
| C3P | 0.01 | 0.02 | 0.00 |
| C4P | 15.83 | 19.74 | 0.00 |
| C5P | 61.58 | 54.17 | 99.86 |
| C6P | 14.48 | 16.73 | 0.00 |
| C7P | 4.06 | 4.97 | 0.00 |
| C8P | 1.31 | 1.59 | 0.00 |
| C9+ | 2.30 | 2.33 | 0.00 |
| C5N | 0.00 | 0.00 | 0.00 |
| C6N | 0.00 | 0.00 | 0.00 |
| C7N | 0.01 | 0.00 | 0.00 |
| C8N | 0.36 | 0.39 | 0.00 |
| C6A | 0.00 | 0.00 | 0.00 |
| C7A | 0.00 | 0.01 | 0.00 |
| C8A | 0.06 | 0.07 | 0.00 |
| nC4-nC5 unknowns | 0.00 | 0.00 | 0.14 |
| mmoles (based on wt. %) | | | |
| C3P | 0 | 0 | 0 |
| C4P | 272 | 340 | 0 |
| C5P | 854 | 751 | 1384 |
| C6P | 168 | 194 | 0 |
| C7P | 41 | 50 | 0 |
| C8P | 11 | 14 | 0 |
| C9+ | 18 | 18 | 0 |
| C5N | 0 | 0 | 0 |
| C6N | 0 | 0 | 0 |
| C7N | 0 | 0 | 0 |
| C8N | 3 | 3 | 0 |
| C6A | 0 | 0 | 0 |
| C7A | 0 | 0 | 0 |
| C8A | 1 | 1 | 0 |
| nC4-nC5 unknowns | 0 | 0 | 2 |
| Total mmoles | 1368 | 1371 | 1386 |

Example 8 iC5—Stir Rate at 700 rpm with [("Bu)$_3$P(Hex)][Al$_2$Cl$_6$Br] in Hastelloy C Autoclave at 55° C.

A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.416 g of [("Bu)$_3$P(Hex)][Al$_2$Cl$_6$Br], and the autoclave head was attached. To the sample cylinder 1.422 g of 2-chloro-2-methylpropane, which had previously been dried over activated sieves, was added. The sample cylinder was closed under nitrogen, and both the autoclave and sample cylinder were removed from the glovebox. The autoclave was charged with 114 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 16 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 140 psi (0.965 MPa), and the autoclave was set to stir at 700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to iso-pentane was 0.40 and the volume ratio was 0.20. The mass rate of reaction was 70, and the volume rate was 140 after 0.5 h. The results of the run are shown in Tables 7 and 8.

TABLE 7

Disproportionation and Isomerization of iso-Pentane at 55° C., 700 rpm, Hastelloy C autoclave, wt. % of reaction mixture

| t (h) | % Conv. | C3− | iC4 | nC4 | iC5 | nC5 | C6P | C7+ | i/n | S. Disp. | $S_{isoparaffin}$ |
|---|---|---|---|---|---|---|---|---|---|---|---|
| 0.5 | 14 | 0.00 | 5.04 | 0.01 | 85.85 | 0.94 | 4.98 | 3.16 | 11.4 | 93 | 82 |
| 2.8 | 38 | 0.14 | 14.04 | 0.11 | 62.48 | 3.13 | 12.89 | 7.08 | 8.1 | 92 | 83 |
| 4.5 | 54 | 0.03 | 20.70 | 0.25 | 46.32 | 4.41 | 16.82 | 11.45 | 7.6 | 92 | 82 |

TABLE 8

| Time (h) | 0.5 | 2.8 | 4.5 | NA |
|---|---|---|---|---|
| Wt. % | | | | feed |
| C3P | 0.00 | 0.14 | 0.03 | 0.00 |
| C4P | 5.05 | 14.16 | 20.94 | 0.00 |
| C5P | 86.79 | 65.61 | 50.73 | 99.86 |
| C6P | 4.99 | 12.88 | 16.83 | 0.00 |
| C7P | 1.19 | 3.60 | 5.73 | 0.00 |
| C8P | 0.38 | 1.15 | 2.05 | 0.00 |
| C9+ | 1.30 | 2.07 | 3.08 | 0.00 |
| C5N | 0.00 | 0.00 | 0.00 | 0.00 |
| C6N | 0.00 | 0.00 | 0.00 | 0.00 |
| C7N | 0.00 | 0.01 | 0.01 | 0.00 |
| C8N | 0.25 | 0.33 | 0.50 | 0.00 |
| C6A | 0.00 | 0.00 | 0.00 | 0.00 |
| C7A | 0.00 | 0.00 | 0.01 | 0.00 |
| C8A | 0.02 | 0.03 | 0.05 | 0.00 |
| nC4-nC5 unknowns | 0.00 | 0.00 | 0.00 | 0.14 |
| mmoles (based on wt. %) | | | | |
| C3P | 0 | 3 | 1 | 0 |
| C4P | 87 | 244 | 360 | 0 |
| C5P | 1203 | 909 | 703 | 1384 |
| C6P | 58 | 150 | 195 | 0 |
| C7P | 12 | 36 | 57 | 0 |
| C8P | 3 | 10 | 18 | 0 |

TABLE 8-continued

| Time (h) | 0.5 | 2.8 | 4.5 | NA |
|---|---|---|---|---|
| C9+ | 10 | 16 | 24 | 0 |
| C5N | 0 | 0 | 0 | 0 |
| C6N | 0 | 0 | 0 | 0 |
| C7N | 0 | 0 | 0 | 0 |
| C8N | 2 | 3 | 4 | 0 |
| C6A | 0 | 0 | 0 | 0 |
| C7A | 0 | 0 | 0 | 0 |
| C8A | 0 | 0 | 1 | 0 |
| nC4-nC5 unknowns | 0 | 0 | 0 | 2 |
| Total mmoles | 1375 | 1371 | 1364 | 1386 |

Example 9 iC5—Stir Rate at 700 rpm with [1-Butyl-1-methylimidazolium][$Al_2Cl_7$] at 55° C. in a Hastelloy C Autoclave A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 55.310 g of [1-butyl-1-methylimidazolium][$Al_2Cl_7$], and the autoclave head was attached. To the sample cylinder 2.311 g of 2-chloro-2-methylpropane, which had previously been dried over activated sieves, was added. The sample cylinder was closed under nitrogen, and both the autoclave and sample cylinder were removed from the glovebox. The autoclave was charged with 111 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 28 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 150 psi (1.034 MPa), and the autoclave was set to stir at 700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to iso-pentane was 0.41 and the volume ratio was 0.20. The mass rate of reaction was 150, and the volume rate was 310 after 0.6 h. The results of the run are shown in Tables 9 and 10.

TABLE 9

Disproportionation and Isomerization of iso-Pentane at 55° C., 700 rpm, with [1-butyl-3-methylimidazolium][Al$_2$Cl$_7$] in a Hastelloy C autoclave, wt. % of reaction mixture

| t (h) | % Conv. | C3− | iC4 | nC4 | iC5 | nC5 | C6P | C7+ | i/n | S. Disp. | $S_{isoparaffin}$ |
|---|---|---|---|---|---|---|---|---|---|---|---|
| 0.6 | 37 | 0.01 | 13.86 | 0.08 | 62.83 | 3.11 | 11.50 | 8.59 | 8.2 | 92 | 80 |
| 1.7 | 69 | 0.04 | 27.55 | 0.56 | 31.04 | 5.47 | 18.18 | 17.15 | 6.9 | 92 | 80 |
| 2.9 | 75 | 0.07 | 31.33 | 1.10 | 24.52 | 5.47 | 18.13 | 19.38 | 6.6 | 93 | 79 |
| 4.5 | 76 | 0.09 | 32.31 | 1.56 | 23.41 | 5.34 | 18.37 | 18.90 | 6.4 | 93 | 80 |

TABLE 10

| Time (h) | 0.6 | 1.7 | 2.9 | 4.5 | NA |
|---|---|---|---|---|---|
| Wt. % | | | | | feed |
| C3P | 0.01 | 0.04 | 0.07 | 0.09 | 0.00 |
| C4P | 13.95 | 28.12 | 32.44 | 33.88 | 0.00 |
| C5P | 65.94 | 36.51 | 29.98 | 28.75 | 99.86 |
| C6P | 11.50 | 18.17 | 18.12 | 18.38 | 0.00 |
| C7P | 3.68 | 7.80 | 8.61 | 8.65 | 0.00 |
| C8P | 1.37 | 3.36 | 4.18 | 4.25 | 0.00 |
| C9+ | 3.01 | 5.09 | 5.43 | 5.09 | 0.00 |
| C5N | 0.00 | 0.00 | 0.00 | 0.00 | 0.00 |
| C6N | 0.00 | 0.00 | 0.00 | 0.00 | 0.00 |
| C7N | 0.01 | 0.01 | 0.01 | 0.01 | 0.00 |
| C8N | 0.45 | 0.84 | 0.93 | 0.86 | 0.00 |
| C6A | 0.00 | 0.00 | 0.00 | 0.00 | 0.00 |
| C7A | 0.00 | 0.03 | 0.04 | 0.04 | 0.00 |
| C8A | 0.08 | 0.06 | 0.23 | 0.06 | 0.00 |
| nC4-nC5 unknowns | 0.00 | 0.00 | 0.00 | 0.00 | 0.14 |
| mmoles (based on wt. %) | | | | | |
| C3P | 0 | 1 | 2 | 2 | 0 |
| C4P | 240 | 484 | 558 | 583 | 0 |
| C5P | 914 | 506 | 416 | 398 | 1384 |
| C6P | 133 | 211 | 210 | 213 | 0 |
| C7P | 37 | 78 | 86 | 86 | 0 |
| C8P | 12 | 29 | 37 | 37 | 0 |
| C9+ | 23 | 40 | 42 | 40 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 4 | 7 | 8 | 8 | 0 |
| C6A | 0 | 0 | 0 | 0 | 0 |
| C7A | 0 | 0 | 0 | 0 | 0 |
| C8A | 1 | 1 | 2 | 1 | 0 |
| nC4-nC5 unknowns | 0 | 0 | 0 | 0 | 2 |
| Total mmoles | 1365 | 1357 | 1361 | 1368 | 1386 |

Example 10 iC5 [("Bu)$_3$P(Hex)][Al$_2$Cl$_6$Br] in Hastelloy C Autoclave at 95° C.

A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.419 g of [("Bu)$_3$P(Hex)][Al$_2$Cl$_6$Br], and the autoclave head was attached. To the sample cylinder 3.680 g of 2-chloro-2-methylpropane, which had previously been dried over activated sieves, was added. The sample cylinder was closed under nitrogen, and both the autoclave and sample cylinder were removed from the glovebox. The autoclave was charged with 102 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 15 g of iso-pentane using the same method described above and then attached to the autoclave. The autoclave was heated to 95° C., and the 2-chloro-2-methylpropane/iso-pentane solution in the sample cylinder was added with an over-pressure of nitrogen. After complete addition, the initial pressure in the autoclave was 165 psi (1.138 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to iso-pentane was 0.46 and the volume ratio was 0.23. The mass rate of reaction was 260, and the volume rate was 520 after 0.6 h. The results of the run are shown in Tables 11 and 12.

TABLE 11

Disproportionation and Isomerization of iso-Pentane at 95° C., wt. % of reaction mixture

| t (h) | % Conv. | C3− | iC4 | nC4 | iC5 | nC5 | C6P | C7+ | i/n | S. Disp. | $S_{isoparaffin}$ | RON | RVP (psi) |
|---|---|---|---|---|---|---|---|---|---|---|---|---|---|
| 0.6 | 72 | 0.37 | 27.78 | 1.72 | 28.32 | 4.2 | 16.21 | 21.36 | 6.3 | 94 | 73 | 80.0 | 12.5 |
| 1.8 | 76 | 0.82 | 31.73 | 3.91 | 23.66 | 5.4 | 17.15 | 17.29 | 4.6 | 93 | 76 | 77.6 | 12.3 |
| 3.1 | 77 | 1.05 | 31.50 | 5.12 | 23.14 | 5.71 | 17.1 | 16.38 | 4.0 | 92 | 74 | ND | ND |
| 4.6 | 77 | 1.21 | 31.56 | 6.14 | 22.79 | 5.90 | 16.91 | 15.42 | 3.7 | 92 | 73 | ND | ND |

TABLE 12

| Time (h) | 0.6 | 1.8 | 3.1 | 4.6 | NA |
|---|---|---|---|---|---|
| Wt. % | | | | | feed |
| C3P | 0.37 | 0.82 | 1.05 | 1.21 | 0.00 |
| C4P | 29.50 | 35.64 | 36.62 | 37.70 | 0.00 |
| C5P | 32.51 | 29.06 | 28.85 | 28.69 | 99.86 |
| C6P | 16.22 | 17.16 | 17.10 | 16.91 | 0.00 |
| C7P | 7.66 | 8.19 | 7.96 | 7.56 | 0.00 |
| C8P | 3.42 | 3.88 | 3.79 | 3.57 | 0.00 |
| C9+ | 9.74 | 4.63 | 4.04 | 3.81 | 0.00 |
| C5N | 0.00 | 0.00 | 0.00 | 0.00 | 0.00 |
| C6N | 0.00 | 0.00 | 0.00 | 0.00 | 0.00 |
| C7N | 0.01 | 0.02 | 0.02 | 0.02 | 0.00 |
| C8N | 0.51 | 0.56 | 0.53 | 0.48 | 0.00 |
| C6A | 0.00 | 0.00 | 0.00 | 0.00 | 0.00 |
| C7A | 0.04 | 0.04 | 0.04 | 0.03 | 0.00 |
| C8A | 0.01 | 0.02 | 0.02 | 0.02 | 0.00 |
| nC4-nC5 unknowns | 0.00 | 0.00 | 0.00 | 0.00 | 0.14 |
| mmoles (based on wt. %) | | | | | |
| C3P | 8 | 19 | 24 | 27 | 0 |
| C4P | 508 | 613 | 630 | 649 | 0 |
| C5P | 451 | 403 | 400 | 398 | 1384 |
| C6P | 188 | 199 | 198 | 196 | 0 |
| C7P | 76 | 82 | 79 | 75 | 0 |
| C8P | 30 | 34 | 33 | 31 | 0 |
| C9+ | 76 | 36 | 31 | 30 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 5 | 5 | 5 | 4 | 0 |
| C6A | 0 | 0 | 0 | 0 | 0 |
| C7A | 0 | 0 | 0 | 0 | 0 |
| C8A | 0 | 0 | 0 | 0 | 0 |
| nC4-nC5 unknowns | 0 | 0 | 0 | 0 | 2 |
| Total mmoles | 1343 | 1391 | 1402 | 1411 | 1386 |

Example 11 nC5 with [("Bu)$_3$P(Hex)][Al$_2$Cl$_6$Br] at 95° C. in a Hastelloy C Autoclave A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.409 g of [("Bu)$_3$P(Hex)][Al$_2$Cl$_6$Br], and the autoclave head was attached. To the sample cylinder 3.679 g of 2-chloro-2-methylpropane, which had previously been dried over activated sieves, was added. The sample cylinder was closed under nitrogen, and both the autoclave and sample cylinder were removed from the glovebox. The autoclave was charged with 102 g of n-pentane from a pressurized feed charger without displacing the nitrogen present in the autoclave. The n-pentane passed over a high surface sodium column to remove any water before entering the autoclave. Similarly, the nitrogen used to pressurize the charger and for all other work passed over a separate high surface sodium column. The sample cylinder was charged with 15 g of n-pentane using the same method described above and then attached to the autoclave. The autoclave was heated to 95° C., and the 2-chloro-2-methylpropane/n-pentane solution in the sample cylinder was added with an over-pressure of nitrogen. After complete addition, the initial pressure in the autoclave was 160 psi (1.103 MPa), and the autoclave was then set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to n-pentane was 0.46 and the volume ratio was 0.24. The mass rate of reaction was 130, and the volume rate was 240 after 1 h. The results of the run are shown in Tables 13 and 14.

TABLE 13

Disproportionation and Isomerization of n-Pentane at 95° C., wt. % of reaction mixture

| t (h) | % Conv. | C3− | iC4 | nC4 | iC5 | nC5 | C6P | C7+ | i/n | S. Disp. | $S_{isoparaffin}$ | $S_{iso-isom}$ |
|---|---|---|---|---|---|---|---|---|---|---|---|---|
| 1.0 | 59 | 0.42 | 18.63 | 1.71 | 19.46 | 41.34 | 10.27 | 8.14 | 16.9 | 67 | 90 | 33 |
| 2.2 | 70 | 0.94 | 22.7 | 3.08 | 20.83 | 29.43 | 12.54 | 10.30 | 12.1 | 70 | 87 | 30 |
| 3.5 | 76 | 0.91 | 25.1 | 4.06 | 21.56 | 23.72 | 13.57 | 11.03 | 10.4 | 72 | 86 | 28 |
| 4.8 | 80 | 1.05 | 26.39 | 4.78 | 21.83 | 20.06 | 14.26 | 11.63 | 9.4 | 73 | 86 | 27 |
| 8.0 | 85 | 1.35 | 27.64 | 6.10 | 21.68 | 14.82 | 14.78 | 12.84 | 8.0 | 74 | 83 | 25 |

TABLE 14

| Time (h) | 1.0 | 2.2 | 3.5 | 4.8 | 8.0 | NA |
|---|---|---|---|---|---|---|
| Wt. % | | | | | | feed |
| C3P | 0.42 | 0.94 | 0.91 | 1.05 | 1.35 | 0.00 |
| C4P | 20.35 | 25.78 | 29.16 | 31.17 | 33.74 | 0.00 |
| C5P | 60.81 | 50.26 | 45.28 | 41.90 | 36.50 | 99.60 |
| C6P | 10.27 | 12.55 | 13.59 | 14.25 | 14.78 | 0.00 |
| C7P | 4.17 | 5.17 | 5.67 | 5.96 | 6.24 | 0.00 |
| C8P | 1.63 | 2.11 | 2.40 | 2.57 | 2.82 | 0.00 |
| C9+ | 2.02 | 2.71 | 2.58 | 2.67 | 4.10 | 0.00 |
| C5N | 0.00 | 0.00 | 0.00 | 0.00 | 0.00 | 0.00 |
| C6N | 0.00 | 0.00 | 0.00 | 0.00 | 0.00 | 0.00 |
| C7N | 0.01 | 0.02 | 0.02 | 0.02 | 0.02 | 0.00 |
| C8N | 0.26 | 0.32 | 0.36 | 0.38 | 0.41 | 0.00 |
| C6A | 0.00 | 0.00 | 0.00 | 0.00 | 0.00 | 0.00 |
| C7A | 0.01 | 0.02 | 0.02 | 0.02 | 0.02 | 0.00 |
| C8A | 0.06 | 0.13 | 0.03 | 0.03 | 0.04 | 0.00 |
| nC4-nC5 unknowns | 0.00 | 0.00 | 0.00 | 0.00 | 0.00 | 0.34 |
| nC5-nC6 unknowns | 0.00 | 0.00 | 0.00 | 0.00 | 0.00 | 0.05 |

TABLE 14-continued

| Time (h) | 1.0 | 2.2 | 3.5 | 4.8 | 8.0 | NA |
|---|---|---|---|---|---|---|
| mmoles (based on wt. %) | | | | | | |
| C3P | 10 | 21 | 21 | 24 | 31 | 0 |
| C4P | 350 | 444 | 502 | 536 | 580 | 0 |
| C5P | 843 | 697 | 628 | 581 | 506 | 1380 |
| C6P | 119 | 146 | 158 | 165 | 172 | 0 |
| C7P | 42 | 52 | 57 | 59 | 62 | 0 |
| C8P | 14 | 18 | 21 | 23 | 25 | 0 |
| C9+ | 16 | 21 | 20 | 21 | 32 | 0 |
| C5N | 0 | 0 | 0 | 0 | 0 | 0 |

2-chloro-2-methylpropane/n-pentane solution in the sample cylinder was added with an over-pressure of nitrogen. After complete addition, the initial pressure in the autoclave was 260 psi (1.793 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to n-pentane was 0.44 and the volume ratio was 0.21. The mass rate of reaction was 220, and the volume rate was 450 after 0.6 h. The results of the run are shown in Tables 15 and 16.

TABLE 15

Disproportionation and Isomerization of n-Pentane at 95° C. with [1-butyl-1-methylpyrrolidinium][Al$_2$Cl$_7$], wt. % of reaction mixture

| t (h) | % Conv. | C3− | iC4 | nC4 | iC5 | nC5 | C6P | C7+ | i/n | S. Disp. | $S_{isoparaffin}$ | $S_{iso\text{-}isom}$ | RON | RVP (psi) |
|---|---|---|---|---|---|---|---|---|---|---|---|---|---|---|
| 0.6 | 57 | 0.49 | 18.16 | 2.44 | 18.55 | 42.87 | 10.02 | 7.48 | 13.0 | 68 | 89 | 32 | ND | ND |
| 1.9 | 84 | 1.22 | 28.59 | 5.73 | 22.01 | 15.60 | 14.75 | 12.00 | 8.7 | 74 | 85 | 26 | 76.1 | 13.5 |
| 3.2 | 89 | 1.70 | 30.42 | 7.70 | 21.66 | 10.57 | 15.38 | 12.54 | 7.1 | 76 | 83 | 24 | 77.1 | 13.2 |
| 4.4 | 91 | 1.96 | 30.79 | 8.72 | 21.31 | 9.06 | 15.51 | 12.65 | 6.5 | 76 | 81 | 23 | 77.4 | 13.0 |

TABLE 14-continued

| Time (h) | 1.0 | 2.2 | 3.5 | 4.8 | 8.0 | NA |
|---|---|---|---|---|---|---|
| C6N | 0 | 0 | 0 | 0 | 0 | 0 |
| C7N | 0 | 0 | 0 | 0 | 0 | 0 |
| C8N | 2 | 3 | 3 | 3 | 4 | 0 |
| C6A | 0 | 0 | 0 | 0 | 0 | 0 |
| C7A | 0 | 0 | 0 | 0 | 0 | 0 |
| C8A | 1 | 1 | 0 | 0 | 0 | 0 |
| nC4-nC5 unknowns | 0 | 0 | 0 | 0 | 0 | 5 |
| nC5-nC6 unknowns | 0 | 0 | 0 | 0 | 0 | 1 |
| Total mmoles | 1396 | 1403 | 1409 | 1413 | 1412 | 1386 |

Example 12 nC5 with [1-butyl-1-methylpyrrolidinium][Al$_2$Cl$_7$] at 95° C.

A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 52.795 g of [1-butyl-1-methylpyrrolidinium][Al$_2$Cl$_7$] and the autoclave head was attached. To the sample cylinder 5.24 g of 2-chloro-2-methylpropane, which had previously been dried over activated sieves, was added. The sample cylinder was closed under nitrogen, and both the autoclave and sample cylinder were removed from the glovebox. The autoclave was charged with 98 g of n-pentane from a pressurized feed charger without displacing the nitrogen present in the autoclave. The n-pentane passed over a high surface sodium column to remove any water before entering the autoclave. Similarly, the nitrogen used to pressurize the charger and for all other work passed over a separate high surface sodium column. The sample cylinder was charged with 33 g of n-pentane using the same method described above and attached to the autoclave. The autoclave was heated to 95° C., and the

TABLE 16

| Time (h) | 0.6 | 1.9 | 3.2 | 4.4 | NA |
|---|---|---|---|---|---|
| Wt. % | | | | | feed |
| C3P | 0.49 | 1.22 | 1.70 | 1.96 | 0.00 |
| C4P | 20.60 | 34.32 | 38.12 | 39.51 | 0.00 |
| C5P | 61.41 | 37.61 | 32.23 | 30.37 | 99.60 |
| C6P | 10.02 | 14.76 | 15.39 | 15.50 | 0.00 |
| C7P | 3.93 | 6.04 | 6.24 | 6.25 | 0.00 |
| C8P | 1.52 | 2.64 | 2.85 | 2.89 | 0.00 |
| C9+ | 1.71 | 2.97 | 3.00 | 3.05 | 0.00 |
| C5N | 0.00 | 0.00 | 0.00 | 0.00 | 0.00 |
| C6N | 0.00 | 0.00 | 0.00 | 0.00 | 0.00 |
| C7N | 0.01 | 0.01 | 0.02 | 0.02 | 0.00 |
| C8N | 0.25 | 0.39 | 0.41 | 0.41 | 0.00 |
| C6A | 0.00 | 0.00 | 0.00 | 0.00 | 0.00 |
| C7A | 0.01 | 0.02 | 0.02 | 0.02 | 0.00 |
| C8A | 0.04 | 0.01 | 0.02 | 0.02 | 0.00 |
| nC4-nC5 unknowns | 0.00 | 0.00 | 0.00 | 0.00 | 0.34 |
| nC5-nC6 unknowns | 0.00 | 0.00 | 0.00 | 0.00 | 0.05 |
| mmoles (based on wt. %) | | | | | |
| C3P | 11 | 28 | 39 | 44 | 0 |
| C4P | 354 | 591 | 656 | 680 | 0 |
| C5P | 851 | 521 | 447 | 421 | 1380 |
| C6P | 116 | 171 | 179 | 180 | 0 |
| C7P | 39 | 60 | 62 | 62 | 0 |
| C8P | 13 | 23 | 25 | 25 | 0 |
| C9+ | 13 | 23 | 23 | 24 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 2 | 4 | 4 | 4 | 0 |
| C6A | 0 | 0 | 0 | 0 | 0 |
| C7A | 0 | 0 | 0 | 0 | 0 |
| C8A | 0 | 0 | 0 | 0 | 0 |
| nC4-nC5 unknowns | 0 | 0 | 0 | 0 | 5 |
| nC5-nC6 unknowns | 0 | 0 | 0 | 0 | 1 |
| Total mmoles | 1402 | 1421 | 1435 | 1441 | 1386 |

Example 13 nC7—Stir Rate at 1700 rpm with [("Bu)$_3$P(Hex)][Al$_2$Cl$_6$Br] at 55° C.-80° C. in a Hastelloy C Autoclave A 300 mL Hastelloy C autoclave, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 50.425 g of [("Bu)$_3$P(Hex)][Al$_2$Cl$_6$Br], 201 mL of n-heptane (pre-dried by storing over activated 3 A MS for several days) and then the autoclave head was attached. The sample cylinder was charged with 8.833 g of a 82.29 wt. % n-heptane and 17.71 wt. % 2-chloro-2-methylpropane mixture, both of which had previously been dried over activated sieves. The sample cylinder was closed under nitrogen, and both the autoclave and sample cylinder were removed from the glovebox. The autoclave was heated to 55° C., and then the 2-chloro-2-methylpropane/n-heptane solution in the sample cylinder was added with an over-pressure of nitrogen. The nitrogen used to provide this overpressure was passed over a high surface sodium column. After complete addition, the initial pressure in the autoclave was 340 psi (2.34 MPa), and the autoclave was set to stir at 1700 rpm. The reaction was monitored by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. After about 24 h, the temperature was increased to 80° C. At the end of the reaction (45 h), an aliquot was sampled directly from the autoclave by opening a valve from the autoclave, passing the paraffinic layer through a SiO$_2$ column, and into a sample cylinder. The sample cylinder was then charged to about 300 psi using nitrogen prior to offline analysis. The mass ratio of liquid catalyst to n-heptane was 0.36 and the volume ratio was 0.20. The mass rate of reaction was 2, and the volume rate was 3 after 45 h. The results of the run are shown in Table 17 and were determined using the UOP980 method offline.

Example 14 nC7—Stir Rate at 1700 rpm with [1-Butyl-1-methylimidazolium][Al$_2$Cl$_7$] at 95° C. in a Hastelloy C Autoclave A 300 mL Hastelloy C autoclave, Hastelloy C baffle, and 50 mL stainless steel sample cylinder were dried in a 110° C. oven for at least 5 h and then placed in a glovebox antechamber and evacuated over night. The autoclave and sample cylinder were then brought into a nitrogen glovebox. The autoclave was charged with 55.335 g of [1-butyl-1-methylimidazolium][Al$_2$Cl$_7$], 211 mL of n-heptane (pre-dried by storing over activated 3 A MS for at least 1 week) and then the autoclave head was attached. The sample cylinder was charged with 15.358 g of a 62.30 wt. % n-heptane and 37.70 wt. % 2-chloro-2-methylpropane mixture, both of which had previously been dried over activated sieves. The sample cylinder was closed under nitrogen, and both the autoclave and sample cylinder were removed from the glovebox. The autoclave was heated to 95° C., and then the 2-chloro-2-methylpropane/n-heptane solution in the sample cylinder was added with an over-pressure of nitrogen. The nitrogen used to provide this overpressure was passed over a high surface sodium column. After complete addition, the initial pressure in the autoclave was 280 psi (1.93 MPa), and the autoclave was set to stir at 1700 rpm. The reaction was monitored by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to n-heptane was 0.40 and the volume ratio was 0.21. The mass rate of reaction was 110, and the volume rate was 210 after 1 h. The results of the run are shown in Tables 18 and 19 and were determined using the UOP690 method. Alternatively, the aliquot could be introduced to a sample cylinder, after passing through the SiO$_2$ column, and analyzed offline. If this method was used, after introduction of the sample to the sample cylinder, the cylinder would then be charged to about 300 psi using nitrogen prior to offline analysis and analyzed using the UOP980 method.

TABLE 17

Disproportionation and Isomerization of n-heptane at 55-80° C., 1700 rpm, with [("Bu)$_3$P(Hex)][Al$_2$Cl$_6$Br] in a Hastelloy C autoclave, wt. % of reaction mixture

| t (h) | % Conv. | C3– | iC4 | nC4 | iC5 | nC5 | C6P | nC7 | C7P | C8P | Heavies | i/n | S. Disp. | S. Isom. C7P |
|---|---|---|---|---|---|---|---|---|---|---|---|---|---|---|
| 0.0 (feed) | NA | 0.00 | 0.00 | 0.00 | 0.04 | 0.00 | 0.00 | 99.25 | 99.55 | 0.00 | | NA | NA | NA |
| 45 | 26 | 0.07 | 3.90 | 0.14 | 3.31 | 0.16 | 2.89 | 73.44 | | | 15.14 | | | |

TABLE 18

Disproportionation and Isomerization of n-heptane at 95° C., 1700 rpm, with [1-butyl-3-methylimidazolium][Al$_2$Cl$_7$] in a Hastelloy C autoclave, wt. % of reaction mixture

| t (h) | % Conv. | C3− | iC4 | nC4 | iC5 | nC5 | C6P | nC7 | C7P | C8P | nC8-nC10 | C10+ | i/n | S. Disp. | S$_{iso\text{-}isom}$ |
|---|---|---|---|---|---|---|---|---|---|---|---|---|---|---|---|
| 0.0 (feed) | NA | 0.00 | 0.00 | 0.00 | 0.04 | 0.00 | 0.00 | 99.25 | 99.55 | 0.00 | | | NA | NA | NA |
| 1.0 | 44 | 0.58 | 7.63 | 0.89 | 7.58 | 0.77 | 7.06 | | 66.21 | 3.26 | 3.07 | 2.43 | 15 | 77 | 22 |

TABLE 19

| Time (h) | 1.0 | NA |
|---|---|---|
| Wt. % | | Feed |
| C3P | 0.58 | 0.00 |
| C4P | 8.52 | 0.00 |
| C5P | 8.35 | 0.04 |
| C6P | 7.06 | 0.00 |
| C7P | 66.21 | 99.55 |
| C8P | 3.26 | 0.00 |
| C9P | 1.62 | 0.00 |
| C10P | 1.40 | 0.00 |
| C10+ | 2.43 | 0.00 |
| C5N | 0.00 | 0.00 |
| C6N | 0.00 | 0.01 |
| C7N | 0.03 | 0.40 |
| C8N | 0.40 | 0.00 |
| C6A | 0.00 | 0.00 |
| C7A | 0.06 | 0.00 |
| C8A | 0.04 | 0.00 |
| nC4-nC5 | 0.00 | |
| nC5-nC6 unknowns | 0.00 | 0.00 |
| mmoles (based on wt. %) | | |
| C3P | 13 | 0 |
| C4P | 147 | 0 |
| C5P | 116 | 1 |
| C6P | 82 | 0 |
| C7P | 661 | 993 |
| C8P | 29 | 0 |
| C9P | 13 | 0 |
| C10P | 10 | 0 |
| C10+ | 16 | 0 |
| C5N | 0 | 0 |
| C6N | 0 | 0 |
| C7N | 0 | 4 |
| C8N | 4 | 0 |
| C6A | 0 | 0 |
| C7A | 1 | 0 |
| C8A | 0 | 0 |
| nC4-nC5 | 0 | |
| nC5-nC6 unknowns | 0 | 0 |
| Total mmoles | 1090 | 998 |

Example 15 nC$_6$—Stir Rate at 1700 rpm with [1-butyl-3-methylimidazolium][Al$_2$Cl$_7$] in Hastelloy B Autoclave at 100° C.

A 300 mL Hastelloy B autoclave equipped with a Hastelloy B baffle, and a 50 mL stainless steel sample cylinder were dried in a 110° C. oven for at least 8 h. The dried autoclave and sample cylinder were then brought into a nitrogen glovebox. The autoclave was charged with 38.34 g of [1-butyl-3-methylimidazolium][Al$_2$Cl$_7$] and 129.4 g of n-hexane, which had previously been dried over activated 3 A molecular sieves, and the autoclave head was attached. The 50 mL sample cylinder was then charged with 4.02 g of 2-chloro-2-methylpropane, which had previously been dried over activated 3 A molecular sieves, and 10.0 g of the n-hexane feed. The sample cylinder was closed under nitrogen, and both the autoclave and the sample cylinder were removed from the glovebox. The composition of the n-hexane feed is listed in Table 20, entry 1. The autoclave was then heated to 100° C. with stirring at 300 rpm for 29 minutes followed by stirring at 93 rpm for 30 minutes until the reaction temperature was reached. After this point, the reaction mixture was at 100° C. and an aliquot was removed for analysis to determine the extent of conversion during the heating process in the absence of added 2-chloro-2-methylpropane. The aliquot was removed directly from the autoclave by opening a valve from the autoclave, passing the paraffinic layer through a SiO$_2$ column, and then directly into a 75 mL stainless steel sample cylinder. The sample cylinder was pressurized with >300 psi (2.07 MPa) nitrogen. The aliquot was measured on the same GC using the same analytical method described below for the subsequent time points listed below (entry 2, Table 20). After the aliquot removal, stirring was stopped, and the 2-chloro-2-methylpropane/n-hexane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature decreased to 96° C. after 6 minutes of stirring, and the pressure was 340 psi (2.34 MPa) within the autoclave. After 6 minutes of reaction, the reaction mixture was analyzed by GC (entry 3, Table 20). During the course of the reaction, the reaction mixture was periodically analyzed online by GC. The pressure within the autoclave varied from 320-340 psi (2.21 to 2.34 MPa) at 100° C. during the course of the reaction. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. The mass ratio of liquid catalyst to hydrocarbon feed was 0.30 and the volume ratio was 0.15 using the following densities: 1.34 g/mL for the liquid catalyst and 0.659 g/mL for n-hexane. The mass reaction rate was 700, and the volume reaction rate was 1400 after 0.1 h.

TABLE 20

Disproportionation and isomerization of n-hexane at 100° C., 1700 rpm, with [1-butyl-3-methylimidazolium][Al$_2$Cl$_7$] in a Hastelloy B autoclave, wt. % of feed and reaction mixture

| Entry | time (h) | C3P | C4P | C5P | nC6 | iC6 | C7P | C8P | C7N | C8N | C8A | nC4-nC5[a] | nC5-nC6[a] | nC6-nC7[a] | nC7-nC8[a] | nC8-nC9[a] | nC9-nC10[a] | nC10+[a] |
|---|---|---|---|---|---|---|---|---|---|---|---|---|---|---|---|---|---|---|
| 1 | NA | 0.00 | 0.00 | 0.00 | 98.02 | 1.34 | 0.60 | 0.00 | 0.00 | 0.00 | 0.00 | 0.03 | 0.00 | 0.00 | 0.00 | 0.00 | 0.00 | 0.01 |
| 2 | 0.0[b] | 0.02 | 0.44 | 0.52 | 95.51 | 2.66 | 0.69 | 0.06 | 0.02 | 0.02 | 0.01 | 0.00 | 0.00 | 0.00 | 0.00 | 0.01 | 0.01 | 0.02 |
| 3 | 0.1 | 0.21 | 3.84 | 4.94 | 75.53 | 9.83 | 3.03 | 0.44 | 0.22 | 0.34 | 0.05 | 0.00 | 0.00 | 0.00 | 0.22 | 0.42 | 0.38 | 0.47 |
| 4 | 1.2 | 0.73 | 12.20 | 13.33 | 45.08 | 14.92 | 6.62 | 1.63 | 0.57 | 0.80 | 0.09 | 0.02 | 0.00 | 0.00 | 0.00 | 1.32 | 1.12 | 1.55 |
| 5 | 4.0 | 0.80 | 13.26 | 14.58 | 38.16 | 15.80 | 7.95 | 2.22 | 0.62 | 1.08 | 0.12 | 0.00 | 0.00 | 0.02 | 0.00 | 1.79 | 1.48 | 2.07 |

[a]Unknowns within these ranges and
[b]Composition of the feed at 100° C. prior to adding tBuCl/n-hexane feed While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A hydrocarbon conversion process comprising:
    isomerizing a hydrocarbon feed comprising normal C$_6$ alkane or branched C$_6$ alkane by contacting the hydrocarbon feed with a liquid catalyst in a reaction zone under isomerization conditions to form a product mixture comprising at least about 5 wt % branched C$_6$ alkanes if the hydrocarbon feed was the normal C$_6$ alkane or at least about 2 wt % normal C$_6$ alkanes if the hydrocarbon feed was the branched C$_6$ alkane in 1 hr based on the normal C$_6$ alkane or branched C$_6$ alkane in the hydrocarbon feed, wherein the liquid catalyst comprises an unsupported ionic liquid and a carbocation promoter comprising a haloalkane, and wherein a mass ratio of liquid catalyst to hydrocarbon feed is less than 0.75:1;
    wherein the ionic liquid comprises an organic cation and an anion and wherein the organic cation is selected from the group consisting of:

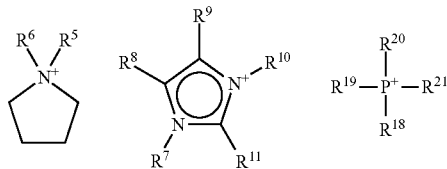

Where R$^5$-R$^{11}$ and R$^{18}$-R$^{21}$ are independently selected from C$_1$-C$_{20}$ hydrocarbons, C$_1$-C$_{20}$ hydrocarbon derivatives, halogens, and H, and x=1-4, or combinations thereof;

wherein the anion is selected from the group consisting of: AlCl$_4^-$, Al$_2$Cl$_7^-$, Al$_3$Cl$_{10}^-$, AlCl$_3$Br$^-$, Al$_2$Cl$_6$Br$^-$, Al$_3$Cl$_9$Br$^-$, AlBr$_4^-$, Al$_2$Br$_7^-$, Al$_3$Br$_{10}^-$, GaCl$_4^-$, Ga$_2$Cl$_7^-$, Ga$_3$Cl$_{10}^-$, GaCl$_3$Br$^-$, Ga$_2$Cl$_6$Br$^-$, Ga$_3$Cl$_9$Br$^-$, CuCl$_2^-$, Cu$_2$Cl$_3^-$, Cu$_3$Cl$_4^-$, ZnCl$_3^-$, FeCl$_3^-$, FeCl$_4^-$, Fe$_3$Cl$_7^-$, PF$_6^-$, BF$_4^-$, or combinations thereof; and wherein the haloalkane comprises 2-chloro-2-methylpropane, 2-chloropropane, 2-chlorobutane, 2-chloro-2-methylbutane, 2-chloropentane, 1-chlorohexane, 3-chloro-3-methylpentane, or combinations thereof; and;
disproportionating the hydrocarbon feed concurrently with the isomerizing of the hydrocarbon feed.

2. The process of claim 1 wherein a molar ratio of the carbocation promoter to ionic liquid is in a range of about 0:1 to about 3:1.

3. The process of claim 1 wherein a residence time in the reaction zone is about 10 hr or less.

4. The process of claim 1 further comprising at least one of: separating the ionic liquid from the product mixture; and separating the carbocation promoter from the product mixture.

5. The process of claim 4 further comprising regenerating the separated ionic liquid.

6. The process of claim 1 further comprising: drying the hydrocarbon feed before contacting the hydrocarbon feed with the liquid catalyst; or treating the hydrocarbon feed to remove one or more of alkenes, dienes, or nitriles; or both.

7. The process of claim 1 wherein a conversion rate for volume is at least about 60 in the absence of an added metal salt.

8. The process of claim 1 wherein a concentration of acid is less than about 2.5 M.

9. The process of claim 1 wherein the product mixture comprises at least about 9 wt % branched C$_6$ alkanes when the hydrocarbon feed was the normal C$_6$ alkane in 1 hr based on the normal C$_6$ alkane in the hydrocarbon feed.

10. The process of claim 1 wherein a selectivity for isoparaffins is at least about 25%, and a conversion is at least about 50%.

11. The process of claim 1 further comprising disproportionating the hydrocarbon feed concurrently with isomerizing the hydrocarbon feed.

12. The process of claim 1 wherein the isomerization conditions include one or more of a temperature in a range of about 0° C. to a decomposition temperature of the ionic liquid, and a pressure in a range of about 0 MPa to about 8.1 MPa.

* * * * *